(12) United States Patent
Kanda et al.

(10) Patent No.: US 8,107,704 B2
(45) Date of Patent: Jan. 31, 2012

(54) IMAGE PROCESSING DEVICE, IMAGE PROCESSING PROGRAM AND IMAGE PROCESSING METHOD

(75) Inventors: Yamato Kanda, Hino (JP); Hiroshi Matsuzaki, Tachikawa (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/621,122

(22) Filed: Nov. 18, 2009

(65) Prior Publication Data

US 2010/0061597 A1    Mar. 11, 2010

Related U.S. Application Data

(63) Continuation of application No. PCT/JP2008/059363, filed on May 21, 2008.

(30) Foreign Application Priority Data

Jun. 5, 2007  (JP) ................................ 2007-149120
Jul. 30, 2007  (JP) ................................ 2007-197298

(51) Int. Cl.
*G06K 9/00* (2006.01)

(52) U.S. Cl. ....................................... 382/128; 128/922

(58) Field of Classification Search .................. 382/100, 382/128, 129, 130, 131, 132; 128/922; 378/4–27
See application file for complete search history.

(56) References Cited

U.S. PATENT DOCUMENTS

| | | | | |
|---|---|---|---|---|
| 6,246,784 B1 * | 6/2001 | Summers et al. | ............. | 382/128 |
| 7,567,692 B2 * | 7/2009 | Buzaglo et al. | ............. | 382/128 |
| 7,684,599 B2 * | 3/2010 | Horn et al. | ..................... | 382/128 |
| 7,747,055 B1 * | 6/2010 | Vining et al. | .................. | 382/131 |
| 7,853,310 B2 * | 12/2010 | Vining et al. | .................. | 600/425 |
| 2003/0077223 A1 | 4/2003 | Glukhovsky et al. | | |
| 2004/0249291 A1 * | 12/2004 | Honda et al. | .................. | 600/476 |
| 2005/0148847 A1 | 7/2005 | Uchiyama et al. | | |
| 2006/0252987 A1 | 11/2006 | Hasegawa et al. | | |

FOREIGN PATENT DOCUMENTS

| | | |
|---|---|---|
| JP | 10-124681 | 5/1998 |
| JP | 2005-198789 | 7/2005 |
| JP | 2005-334331 | 12/2005 |
| JP | 2006-334297 | 12/2006 |

OTHER PUBLICATIONS

International Search Report dated Jul. 29, 2008.

* cited by examiner

*Primary Examiner* — Anand Bhatnagar
(74) *Attorney, Agent, or Firm* — Scully, Scott, Murphy & Presser, P.C.

(57) ABSTRACT

An image processing device for processing time-series intraluminal images captured by an imaging device moving in an in-vivo lumen. The image processing device includes a structural area extracting unit that extracts a structural area from the intraluminal image; a corresponding area extracting unit that extracts a corresponding area corresponding to the structural area from the intraluminal image at a second time point different from a first time point at which the structural area is extracted; a lumen deep portion extracting unit that extracts a lumen deep portion, on which a deep portion in the lumen is captured, from the intraluminal image; and a movement amount estimating unit that estimates a movement amount of the imaging device based on positions of the structural area, the corresponding area and the lumen deep portion.

12 Claims, 26 Drawing Sheets

FIG.18

| | | | | IMAGE AREA |
|---|---|---|---|---|
| $F_{11}$ | $F_{12}$ | ... | $F_{1M-1}$ | $F_{1M}$ |
| $F_{21}$ | ⋱ | | | ⋮ |
| ⋮ | | ⋱ | | ⋮ |
| $F_{N-11}$ | | | ⋱ | ⋮ |
| $F_{N1}$ | ... | ... | ... | $F_{NM}$ |

IMAGE PROCESSING DEVICE, IMAGE PROCESSING PROGRAM AND IMAGE PROCESSING METHOD

CROSS-REFERENCE TO RELATED APPLICATIONS

This application is a continuation of PCT international application Ser. No. PCT/JP2008/059363 filed on May 21, 2008 which designates the United States, incorporated herein by reference, and which claims the benefit of priority from Japanese Patent Applications No. 2007-149120, filed on Jun. 5, 2007, and No. 2007-197298, filed on Jul. 30, 2007, incorporated herein by reference.

BACKGROUND OF THE INVENTION

1. Field of the Invention

The present invention relates to an image processing device, an image processing program and an image processing method for processing time-series images captured by a moving imaging device.

2. Description of the Related Art

In recent years, a medical imaging device for sequentially capturing time-series intraluminal images while moving an in-vivo lumen such as a digestive tract has been developed as represented by a capsule endoscope. The imaging device is swallowed from a mouth of a patient, thereafter moves in lumens by peristaltic action or the like and sequentially captures images to transmit to a receiving device outside the body, and is finally excreted to outside the body.

Conventionally, an image processing device for analyzing a state of an object using time-series images obtained by an imaging device such as a capsule endoscope is known (see U.S. Patent Application Publication No. 2003/0077223). The image processing device compares the time-series images continuously captured by the imaging device, which moves in a gastrointestinal tract, to analyze mobility of the gastrointestinal tract. Specifically, the intra-gastrointestinal tract images are compared, action of the object itself and action of the capsule endoscope are analyzed, and the peristaltic action of the gastrointestinal tract is analyzed.

Images obtained by capturing the inside of in-vivo lumens (intraluminal images) are used not only for checking the mobility of the gastrointestinal tract but also for finding a lesion in the lumen such as the gastrointestinal tract. For example, a doctor observes the time-series intraluminal images, which are received by a receiving device outside the body, using a diagnostic workstation and the like. When a diseased site is found, the doctor performs a medical treatment, such as a tissue collection, arrest of bleeding, or resection of the diseased site, by inserting a medical treatment tool again in the body of the patient, or dissecting the body of the patient as needed. In order to efficiently perform such medical treatment, information that indicates a position of a target diseased site in the lumen is required. When the imaging device captures the diseased site, the position of the imaging device at the time of capturing corresponds to the position of the diseased site or the vicinity thereof. Therefore, when the position of the imaging device at the time of capturing is gasped, the position of the diseased site can be estimated.

As the information regarding the position of the imaging device at the time of capturing, information that shows a position of capturing relative to an entrance or an exit of the lumen or relative to a starting or an ending position of a specific organ along the lumen is more useful than information that shows a spatial coordinate in the body. For example, in a case of an organ that changes its shape in the body, such as a small intestine, even when the position of the imaging device at the time of capturing is grasped by the coordinate, the specified position and an actual position of the diseased site do not conform to each other when the organ has changed its shape. When the position of the imaging device at the time of capturing is grasped by the distance from a base point, such as the entrance of the lumen, the position of the diseased site can be known even when the organ has changed its shape. Also, it is important to know the distance between the lesion and the entrance or the exit of the lumen such as the gastrointestinal tract in order to determine a treatment policy. To calculate the movement amount of the capsule endoscope in the lumen from the predetermined position, detecting a magnetic field generated by a single-core coil, which has generated the magnetic field and is provided in an imaging device, by a plurality of coils arranged outside the body is known (see Japanese Patent Application Laid-open No. 2005-198789).

SUMMARY OF THE INVENTION

An image processing device according to an aspect of the present invention for processing time-series intraluminal images captured by an imaging device moving in an in-vivo lumen includes a structural area extracting unit that extracts a structural area from the intraluminal image; a corresponding area extracting unit that extracts a corresponding area corresponding to the structural area from the intraluminal image at a second time point different from a first time point at which the structural area is extracted; a lumen deep portion extracting unit that extracts a lumen deep portion, on which a deep portion in the lumen is captured, from the intraluminal image; and a movement amount estimating unit that estimates a movement amount of the imaging device based on positions of the structural area, the corresponding area and the lumen deep portion.

An image processing device according to another aspect of the present invention includes an imaging device movement amount estimating unit that processes time-series intraluminal images captured by an imaging device moving in an in-vivo lumen and estimates a movement amount of the imaging device.

An image processing program according to still another aspect of the present invention is an image processing program that, when executed by a computer for processing time-series intraluminal images captured by an imaging device moving in an in-vivo lumen, causes the computer to perform a structural area extracting process that extracts a structural area from the intraluminal image; a corresponding area extracting process that extracts a corresponding area corresponding to the structural area from the intraluminal image at a second time point different from a first time point at which the structural area is extracted; a lumen deep portion extracting process that extracts a lumen deep portion, on which a deep portion in the lumen is captured, from the intraluminal image; and a movement amount estimating process that estimates a movement amount of the imaging device based on positions of the structural area, the corresponding area and the lumen deep portion.

An image processing program according to still another aspect of the present invention is an image processing program that, when executed by a computer, causes the computer to perform an imaging device movement amount estimating process that processes time-series intraluminal images captured by an imaging device moving in an in-vivo lumen to estimate a movement amount of the imaging device; and a position estimating process that accumulates a plurality of values of the movement amount estimated by processing a plurality of the intraluminal images by the imaging device movement amount estimating process, thereby estimating a position of the imaging device in the lumen at each time when capturing each intraluminal image.

An image processing method according to still another aspect of the present invention for processing time-series intraluminal images captured by an imaging device moving in an in-vivo lumen includes a structural area extracting step that extracts a structural area from the intraluminal image; a corresponding area extracting step that extracts a corresponding area corresponding to the structural area from the intraluminal image at a second time point different from a first time point at which the structural area is extracted; a lumen deep portion extracting step that extracts a lumen deep portion, on which a deep portion in the lumen is captured, from the intraluminal image; and a movement amount estimating step that estimates a movement amount of the imaging device based on positions of the structural area, the corresponding area and the lumen deep portion.

An image processing method according to still another aspect of the present invention includes an imaging device movement amount estimating step that processes time-series intraluminal images captured by an imaging device moving in an in-vivo lumen to estimate a movement amount of the imaging device; and a position estimating step that accumulates a plurality of values of the movement amount estimated by processing a plurality of the intraluminal images by the imaging device movement amount estimating step, thereby estimating a position of the imaging device in the lumen at each time when capturing each intraluminal image.

An image processing device according to still another aspect of the present invention for analyzing images of a row of images captured in time series by a moving imaging device includes a movement amount calculating unit that calculates a positional displacement of an object on an image area using correlation between images, and calculates a movement amount the imaging device moves between captures of the images based on the positional displacement; and a distance calculating unit that calculates a movement distance of the imaging device by accumulating and adding the movement amounts.

An image processing program according to still another aspect of the present invention is an image processing program that, when executed by a computer for analyzing images of a row of images captured in time series by a moving imaging device, causes the computer to perform a movement amount calculating process that calculates a positional displacement of an object on an image area using correlation between images, and calculates a movement amount the imaging device moves between captures of the images based on the positional displacement; and a distance calculating process that calculates a movement distance of the imaging device by accumulating and adding the movement amounts.

An image processing method according to still another aspect of the present invention for analyzing images of a row of images captured in time series by a moving imaging device includes a movement amount calculating step that calculates a positional displacement of an object on an image area using correlation between images, and calculates a movement amount the imaging device moves between captures of the images based on the positional displacement; and a distance calculating step that calculates a movement distance of the imaging device by accumulating and adding the movement amounts.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 18 is a view showing an example of division of an image area;

DETAILED DESCRIPTION OF THE PREFERRED EMBODIMENTS

Figure 1:
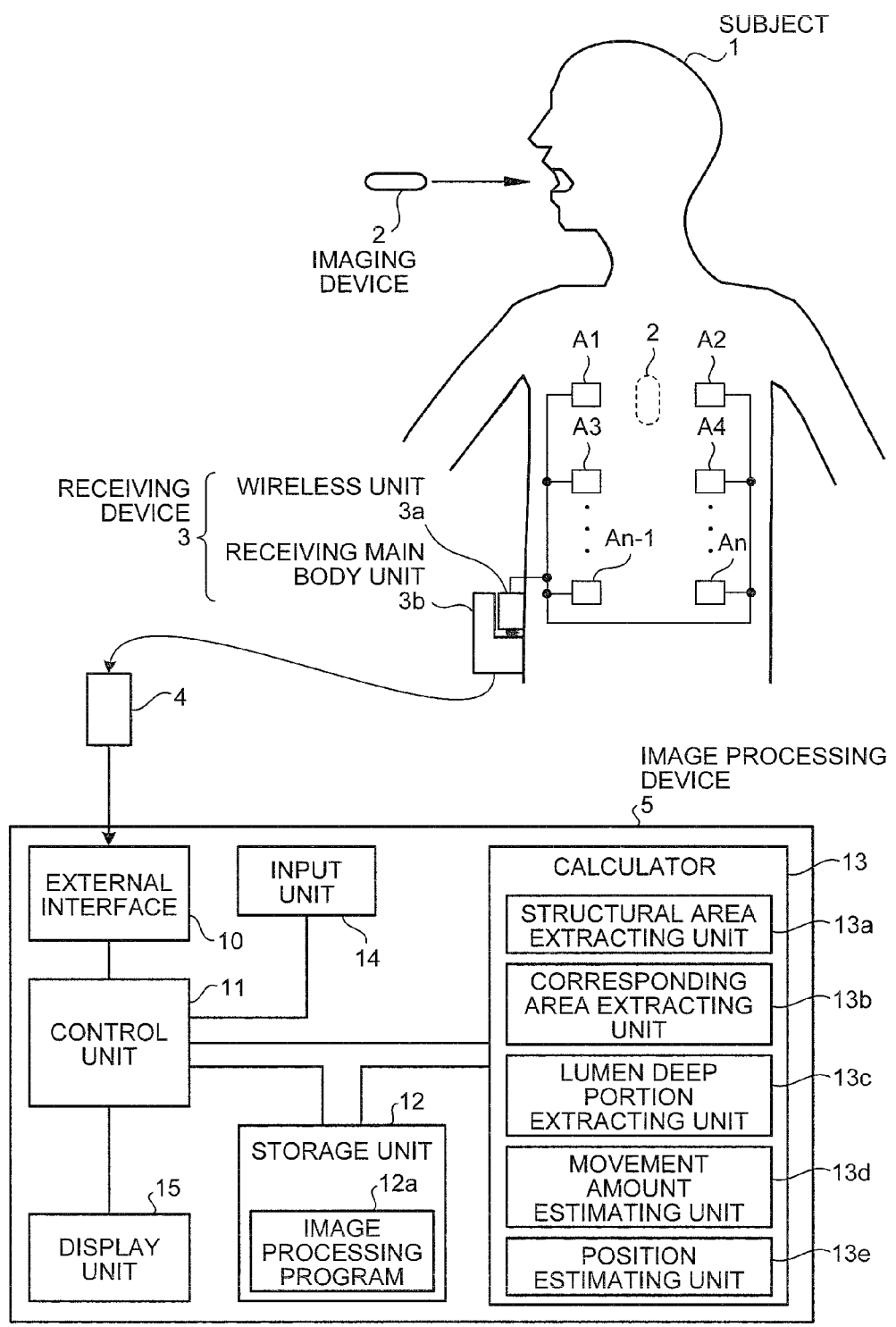
FIG. 1 is an outline schematic diagram showing an entire configuration of an image processing system including an image processing device according to a first embodiment.

Hereinafter, image processing devices, which are best modes for carrying out the present invention, will be described with reference to drawings. Incidentally, the present invention is not limited by each embodiment. Further, the same reference numerals are given to the same or corresponding parts in the drawings.

First Embodiment

FIG. 1 is an outline schematic diagram showing an entire configuration of an image processing system including an image processing device according to a first embodiment. In the first embodiment, a capsule endoscope is used as an example of an imaging device for capturing an image of an in-vivo lumen (hereinafter, referred to as an intraluminal image). The capsule endoscope is provided with a capturing function, a wireless function and an illumination function for illuminating a capturing region. The capsule endoscope is swallowed from a mouth of a subject such as a human and an animal to be inserted into the subject for an examination, for example. Then, the capsule endoscope sequentially captures to acquire the intraluminal images in an esophagus, a stomach, a small intestine, a large intestine and the like, and wirelessly transmits them outside a body until being naturally excreted.

As shown in FIG. 1, the image processing system is provided with an imaging device (capsule endoscope) 2 for capturing the intraluminal images in a subject 1, a receiving device 3 for receiving intraluminal image data wirelessly transmitted from the imaging device 2, an image processing device 5 for processing the intraluminal images captured by the imaging device 2 based on the intraluminal images received by the receiving device 3, and the like. A recording medium that is portable (portable recording medium) 4 is used, for example, for communicating the intraluminal image data between the receiving device 3 and the image processing device 5.

The receiving device 3 is provided with a wireless unit 3a for receiving wireless signals transmitted from the imaging device 2 through a group of receiving antennas A1 to An attached to an outer surface of the body of the subject 1 and a receiving main body unit 3b for processing the wireless signals received by the wireless unit 3a. The wireless unit 3a and the receiving main body unit 3b are detachably connected through a connector and the like. The receiving device 3 is constructed such that the portable recording medium 4 can be attached to and detached from the same, and receives the image data of the intraluminal images in the subject 1 captured by the imaging device 2 in order to accumulate the image data in the portable recording medium 4 in a time-series order. In the first embodiment, it is assumed that the image data of the intraluminal images captured during a time period from time t(0) at an entrance of the lumen to time t(T) at an exit of the lumen is accumulated in the portable recording medium 4 in the time-series order. Herein, the time t(0) at the entrance of the lumen corresponds to the time at which the imaging device 2 is inserted into the subject, and the time t(T) at the exit of the lumen corresponds to the time at which the imaging device 2 is excreted from the body.

The image processing device 5 is provided with an external interface 10, to which the portable recording medium 4 is detachably attached for acquiring the image data of the intraluminal images accumulated in the portable recording medium 4, a control unit 11 for controlling an operation of the entire image processing device 5, a storage unit 12, a calculator 13 for performing various calculation processes for estimating a position of the imaging device 2 at the time of capturing the intraluminal image based on the image, an input unit 14 for inputting various pieces of instruction information, and a display unit 15 for display outputting a calculation result of the calculator 13.

The storage unit 12 is constructed, for example, by various IC memories such as a flash memory capable of updating and storing, such as a ROM and a RAM, an information storage medium such as a hard disk and a CD-ROM incorporated or connected by a data communication terminal, and a reading device. The storage unit 12 stores a program relating to the operation of the image processing device 5, a program for realizing various functions of the image processing device 5, data relating to the execution of the programs and the like. Also, an image processing program 12a for the calculator 13 to process the intraluminal images to estimate the position of the imaging device 2 at the time of capturing is stored.

The calculator 13 is provided with a structural area extracting unit 13a, a corresponding area extracting unit 13b, a lumen deep portion extracting unit 13c, a movement amount estimating unit 13d and a position estimating unit 13e. The structural area extracting unit 13a extracts a structural area from one intraluminal image captured by the imaging device 2, which moves in the lumen. The corresponding area extracting unit 13b extracts a corresponding area corresponding to the structural area extracted from one intraluminal image by the structural area extracting unit 13a, from another intraluminal image captured at time different from the time of the one intraluminal image. The lumen deep portion extracting unit 13c extracts a lumen portion located further in a moving direction of the imaging device 2 (hereinafter, referred to as a "lumen deep portion") from one intraluminal image. The movement amount estimating unit 13d estimates a movement amount of the imaging device 2, which moves from the time at which one intraluminal image is captured to the time at which another intraluminal image is captured, based on positional relationship between the structural area in one intraluminal image, the corresponding area in another intraluminal image and the lumen deep portion. The position estimating unit 13e estimates the position of the imaging device 2 in the lumen when each intraluminal image is captured, based on the movement amount of the imaging device 2 estimated by the movement amount estimating unit 13d.

Figure 2:
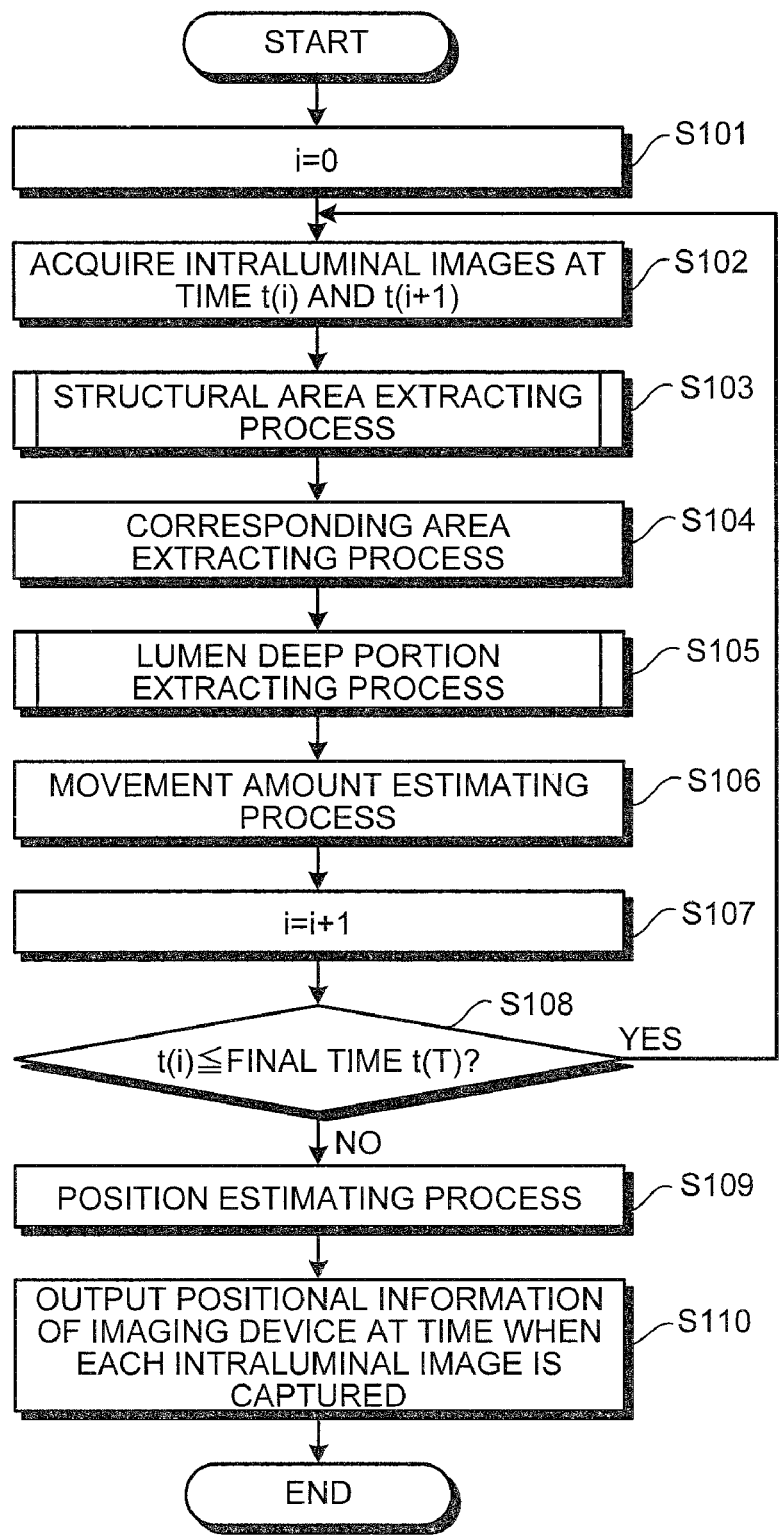
FIG. 2 is an entire flow chart showing a calculation procedure performed by a calculator of the image processing device according to the first embodiment.

FIG. 2 is an entire flow chart showing a calculation procedure performed by the calculator 13 of the image processing device 5. Incidentally, the process herein described is realized by executing the image processing program 12a stored in the storage unit 12 by the calculator 13.

As shown in FIG. 2, the calculator 13 first initializes a symbol i, which indicates the time-series order of the intraluminal images that are processing targets, to "0" (step S101). Then, the calculator 13 acquires through the external interface 10 and the control unit 11 the intraluminal images that are the processing targets at the time t(i) and at the time t(i+1), which is the intraluminal image subsequent to the above-mentioned intraluminal image in time series (step S102). Although the time-series continuous intraluminal images are acquired herein, it is not necessarily required to acquire the time-series continuous intraluminal images when a common part in the lumen is captured in both intraluminal images. Also, when there is distortion in the intraluminal image captured by the imaging device 2, processes at step S103 and subsequent steps may be executed using intraluminal images obtained by correcting the distortion.

Figure 3:
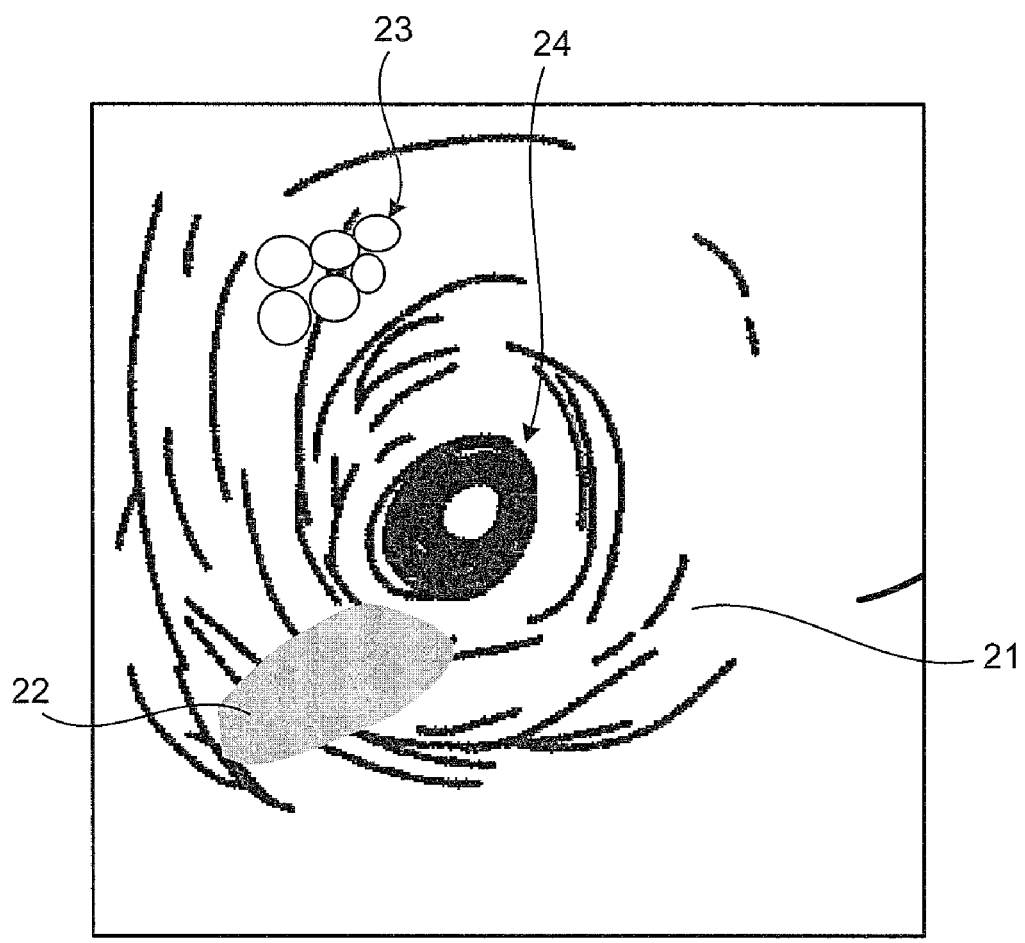
FIG. 3 is a view showing an example of an intraluminal image captured by an imaging device.

FIG. 3 is a view showing an example of the intraluminal image captured by the imaging device 2. In the intraluminal image, a lumen deep portion 24 located further in the moving direction of the imaging device 2 is captured in addition to a mussel membrane in the lumen (hereinafter, referred to as a "luminal mucosal membrane") 21, contents 22 and bubbles 23 floating in the lumen. Incidentally, the intraluminal image captured by the imaging device 2 is a color image having a pixel level (pixel value) for each color component of red (R), green (G) and blue (B) in each pixel position.

Then, as shown in FIG. 2, the structural area extracting unit 13a executes a structural area extracting process for extracting the structural area from the intraluminal image at the time t(i) (step S103), the corresponding area extracting unit 13b executes a corresponding area extracting process for extracting the corresponding area from the intraluminal image at the time t(i+1) (step S104), the lumen deep portion extracting unit 13c executes a lumen deep portion extracting process for extracting the lumen deep portion from each intraluminal image at the time t(i) and t(i+1) (step S105), and the movement amount estimating unit 13d executes a movement amount estimating process for estimating the movement amount of the imaging device 2 from the time t(i) to the time t(i+1) (step S106).

Then, after the movement amount estimating process at step S106, the calculator 13 increments the symbol indicating the time-series order to i=i+1 (step S107) and determines existence or nonexistence of the intraluminal image at the time t(i) being a next processing target using t(i)≦t(T). Herein, t(T) is the final time relating to the intraluminal image being the processing target. In a case of t(i)≦t(T) (step S108: Yes), the processes from step S101 to step S107 are executed again. Incidentally, when processing the time-series continuous intraluminal images, by holding the lumen deep portion extracted from the intraluminal image at the time t(i+1) by the lumen deep portion extracting process at step S105 in the storage unit 12, this may be used when subsequently executing the processes from step S102 to step S107 again by setting the intraluminal image at the time t(i+1) as the intraluminal image at the time t(i), thereby reducing a load of calculation. In contrast, in a case of t(i)>t(T) (step S108: No), the procedure proceeds to step S109, and the position estimating unit 13e executes a position estimating process for estimating the position of the imaging device 2 at each time when each intraluminal image is captured (step S109). Then, the calculator 13 outputs positional information of the imaging device 2 in the lumen at each time when each intraluminal image is captured based on a result of the position estimating process (step S110), and terminates the calculation process of the calculator 13 in the image processing device 5. For example, the calculator 13 causes the display unit 15 to display-output the positional information through the control unit 11.

Next, the processes executed by each part of the calculator 13 are described in detail. First, the structural area extracting process at step S103 in FIG. 2 is described. In this structural area extracting process, the structural area extracting unit 13a extracts a plurality of structural areas from the intraluminal image at the time t(i). The structural area is an area with which the intraluminal images captured at different times (in this process, the intraluminal image at the time t(i) acquired at step S102 in FIG. 2 and the intraluminal image at the time t(i+1), which is time-series continuous with the above-mentioned intraluminal image) can be associated to each other. The structural area is, for example, the area in which a structure, which characterizes a local region on the luminal mucosal membrane (hereinafter, referred to as a "feature structure") is captured. In general, there are wrinkles on the luminal mucosal membrane, and blood vessels are generally partly seen through a surface thereof. The wrinkles on the luminal mucosal membrane and the blood vessels seen through the surface thereof have specific shapes in each part and can be distinguished from those of other parts. Thus, they can be said to be feature structures. The structural area extracting unit 13a extracts the areas in which the feature structures are clearly captured.

Figure 4:
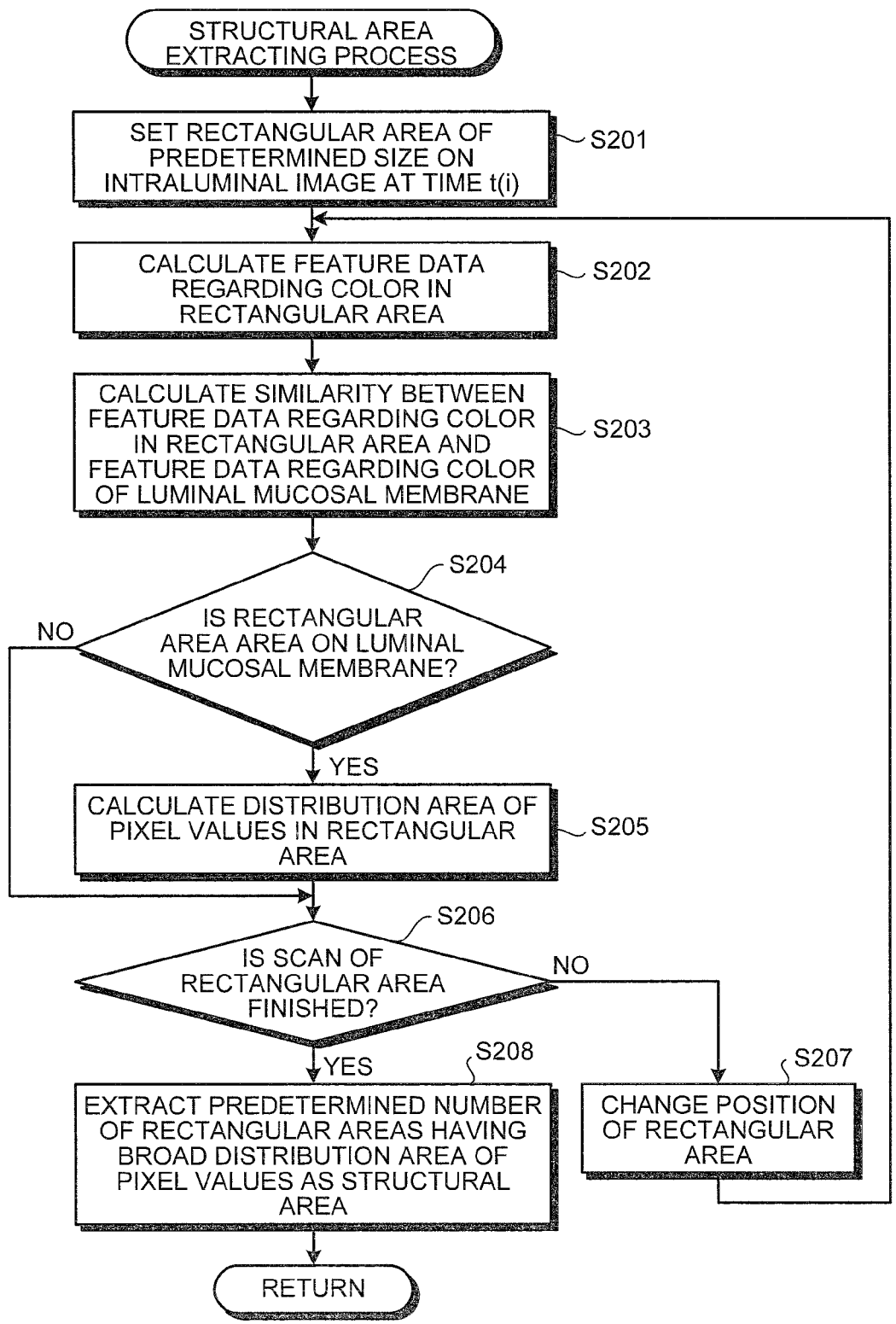
FIG. 4 is a flow chart showing a detailed procedure of a structural area extracting process.

FIG. 4 is a flow chart showing a detailed procedure of the structural area extracting process. For example, the structural area extracting unit 13a sets a rectangular area of a predetermined size at an upper-left position of the intraluminal image at the time t(i) as an initial position, and scans to a lower-right position of the intraluminal image while shifting the position of the rectangular area by a predetermined amount, thereby searching structural areas in the intraluminal image at the time t(i).

First, the structural area extracting unit 13a sets the rectangular area of the predetermined size at the initial position on the intraluminal image at the time t(i) (step S201). Then, the structural area extracting unit 13a calculates feature data regarding a color in the set rectangular area (step S202). Herein, the feature data regarding the color is, for example, an RGB average value or an RGB histogram in the set rectangular area. Alternatively, the feature data regarding the color is an average value or a histogram of a color ratio, color difference, a color phase, or saturation, each of which is secondarily calculated from an RGB value of each pixel in the rectangular area.

Next, the structural area extracting unit 13a calculates similarity between the feature data regarding the color in the rectangular area obtained at step S202 and feature data regarding the color of the luminal mucosal membranes set in advance (step S203). For example, the structural area extracting unit 13a calculates a distance between vector endpoints or a cosine of an angle between vectors in a case in which each feature data is considered as one feature vector, as the similarity.

Next, the structural area extracting unit 13a compares the similarity calculated at step S203 and reference similarity set as a threshold in advance, and determines whether the set rectangular area is the area on the luminal mucosal membrane. For example, when the calculated similarity is not smaller than the reference similarity, the structural area extracting unit 13a determines that the set rectangular area is the area in which the luminal mucosal membrane is captured (step S204: Yes), and the procedure proceeds to step S205. In contrast, when the calculated similarity is smaller than the reference similarity, it is determined that the set rectangular area is the area in which the contents or the bubble are captured, for example, and is not the area in which the luminal mucosal membrane is captured (step S204: No), and the procedure proceeds to step S206.

At step S205, the structural area extracting unit 13a calculates a distribution area of the pixel values in the rectangular area. The calculated distribution area is associated with information relating to the position of the rectangular area at the present time to be held in the storage unit 12. As the distribution area of the pixel values, distribution areas of the pixel values for each RGB color component in the rectangular area may be calculated and the broadest distribution area may be selected from them, or the distribution area of a specific color component may be calculated. When the obtained distribution area is narrow, the pixel values in the rectangular area are in a uniform state, and a possibility that the feature structure is captured is low. In contrast, when the obtained distribution area is broad, the possibility that the feature structure is captured in the rectangular area is high. Incidentally, it is not required to calculate the distribution area of the pixel values using all the pixels in the rectangular area. For example, the distribution area may be calculated using the pixel values of a row of pixels in a predetermined direction in the rectangular area, or the distribution area may be calculated using the pixel values of the rows of pixels in two directions orthogonal to each other, and as a result, the load of calculation can be reduced as compared to a case of calculating using all the pixels in the rectangular area.

Then, the structural area extracting unit 13a changes the position of the rectangular area (step S207) to repeatedly execute the processes from step S202 to step S206 until the scan of the set area on the intraluminal image at the time t(i) is finished (step S206: No). When the scan of the set area on the intraluminal image at the time t(i) is finished (step S206: Yes), the procedure proceeds to step S208. At step S208, the structural area extracting unit 13a extracts a predetermined number of rectangular areas from the rectangular areas, for which distribution areas are calculated at step S205. The predetermined number of rectangular areas includes one rectangular area that has the broadest distribution area and other rectangular areas that are selected in the descending order of the broadness of the distribution area. They are extracted as the structural areas, in which the feature structures are captured. At that time, the rectangular areas are selected such that the structural areas are not overlapped with each other. Data relating to the selected structural areas is held in the storage unit 12. Then, the structural area extracting unit 13a returns the procedure to step S103 in FIG. 2.

Figure 5:
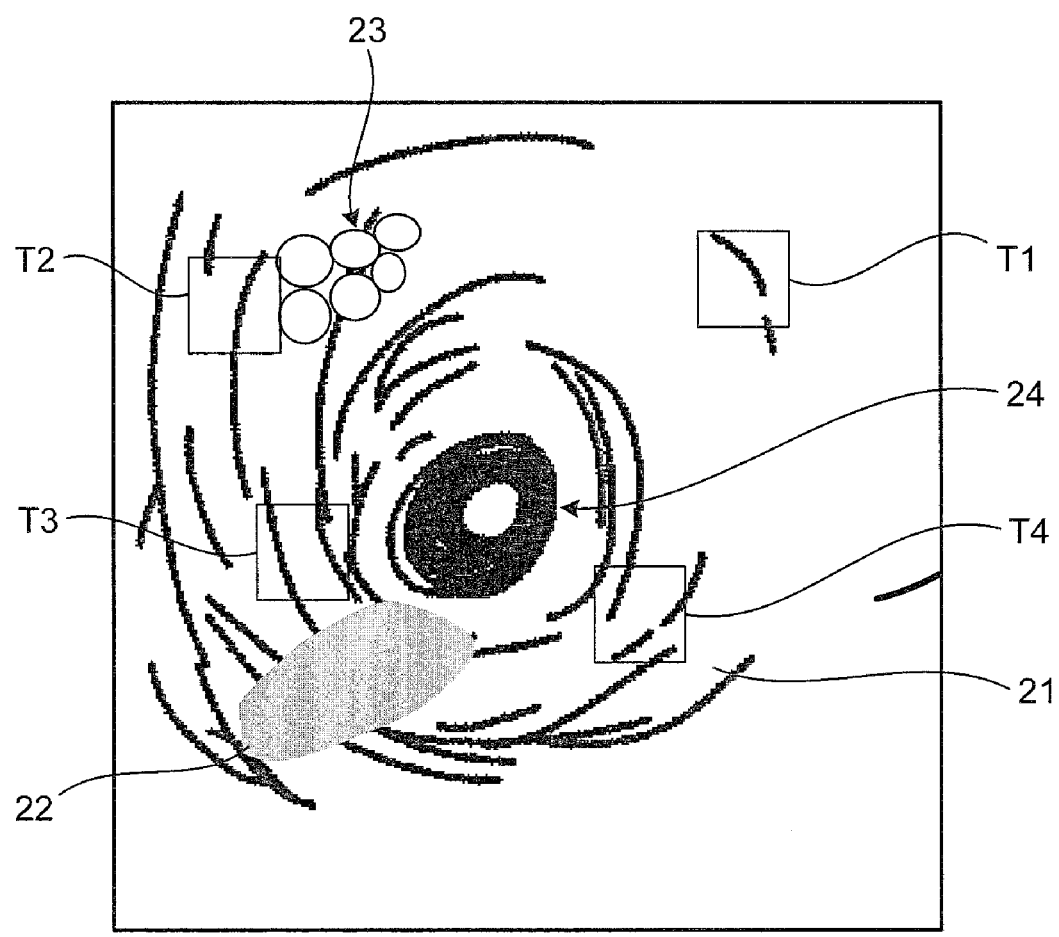
FIG. 5 is a schematic diagram showing a result of the structural area extracting process.

FIG. 5 is a schematic diagram showing a result of the structural area extracting process, and shows examples of the structural areas extracted as the result of the structural area extracting process by setting the intraluminal image illustrated in FIG. 3 as the intraluminal image at the time t(i). In the example in FIG. 5, four structural areas T1, T2, T3 and T4 are extracted as the structural areas, and the structural area in which the feature structure of an area 21 of the luminal mucosal membrane including the wrinkles and blood vessels is captured is extracted while avoiding the areas in which the contents 22 and the bubbles 23 floating in the lumen are captured, by the structural area extracting process.

Next, the corresponding area extracting process at step S104 in FIG. 2 is described. In the corresponding area extracting process, the corresponding area extracting unit 13b extracts an area determined to be the same portion as each structural area extracted from the intraluminal image at the time t(i) as the result of the structural area extracting process, as the corresponding area, from the intraluminal image at the time t(i+1). Specifically, the corresponding area extracting unit 13b sets each structural area extracted by the structural area extracting process as a template, and performs a well-known template matching process to detect the area similar to each template from the intraluminal image at the time t(i+1). As a method of the template matching, for example, the method disclosed in "Digital Image Processing, CG-ARTS Society, 202 p, Template Matching" may be used. Incidentally, a search area of the matching may be set around a central coordinate $(x_j, y_j)$ (j=1, 2, ..., N (N: the number of templates)) of each template in consideration of a time-series change amount of the intraluminal image. Also, a coarse-to-fine search method or a sequential similarity detection algorithm may be used for increasing the speed. For example, the method disclosed in "Digital Image Processing, CG-ARTS Society, 206 p, High-Speed Search Method" may be used. As a result, a coordinate $(x_j', y_j')$ of the most similar area and similarity thereof can be acquired from the intraluminal image at the time t(i+1) for each template corresponding to each structural area extracted from the intraluminal image at the time t(i). As for the template, of which similarity at the time of matching is low, the area is not determined to be the same portion and is not extracted as the corresponding area. Also, the structural area, of which a corresponding area is not extracted as a result of the matching, is not used in subsequent processes.

Figure 6:
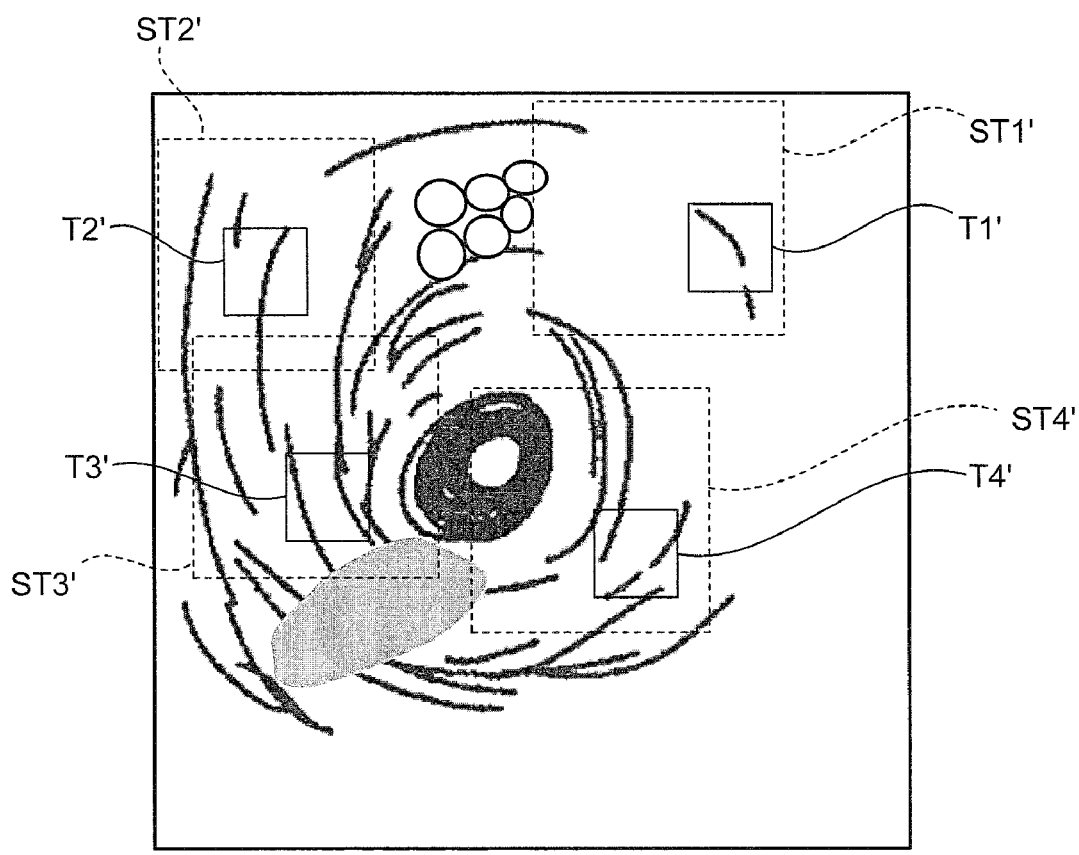
FIG. 6 is a schematic diagram showing a result of a corresponding area extracting process.

FIG. 6 is a schematic diagram showing a result of the corresponding area extracting process, which shows examples of the corresponding areas extracted as the result of the matching by setting each structural area T1 to T4 as the template using the intraluminal image at the time t(i+1) continuous with the intraluminal image illustrated in FIG. 5 in time series. In the examples shown in FIG. 6, corresponding areas T1', T2', T3' and T4' corresponding to the structural areas T1, T2, T3 and T4 in FIG. 5, respectively, are extracted. Also, in FIG. 6, search areas ST1' to ST4' of each template are indicated by dotted lines. Taking the structural area T1 in the intraluminal image at the time t(i) shown in FIG. 5 as an example, the matching by setting the structural area T1 as the template is performed within the search area ST1' indicated by the dotted line in the intraluminal image at the time t(i+1) shown in FIG. 6, and the detected area with high similarity is extracted as the corresponding area T1'.

Next, the lumen deep portion extracting process at step S105 in FIG. 2 is described. In the lumen deep portion extracting process, the lumen deep portion extracting unit 13c extracts the lumen deep portion from each of the intraluminal images at the time t(i) and t(i+1), and calculates a barycentric position thereof. The lumen deep portion is distant from the imaging device 2, so that the illumination from the imaging device 2 hardly reaches, and thus is acquired as a dark area. The area in which dark pixels are gathered is extracted as the lumen deep portion, and the barycentric position thereof is obtained. Incidentally, although a center of the lumen deep portion is schematically brightly shown for easier understanding of the lumen in the intraluminal images shown in FIGS. 3, 5 and 6, actually, the center portion is also dark. The lumen deep portion extracting unit 13c extracts the area in which the dark pixels are gathered (dark portion) from each of the intraluminal images at the time t(i) and t(i+1) as the lumen deep portion, and obtains the barycentric position thereof.

Figure 7:
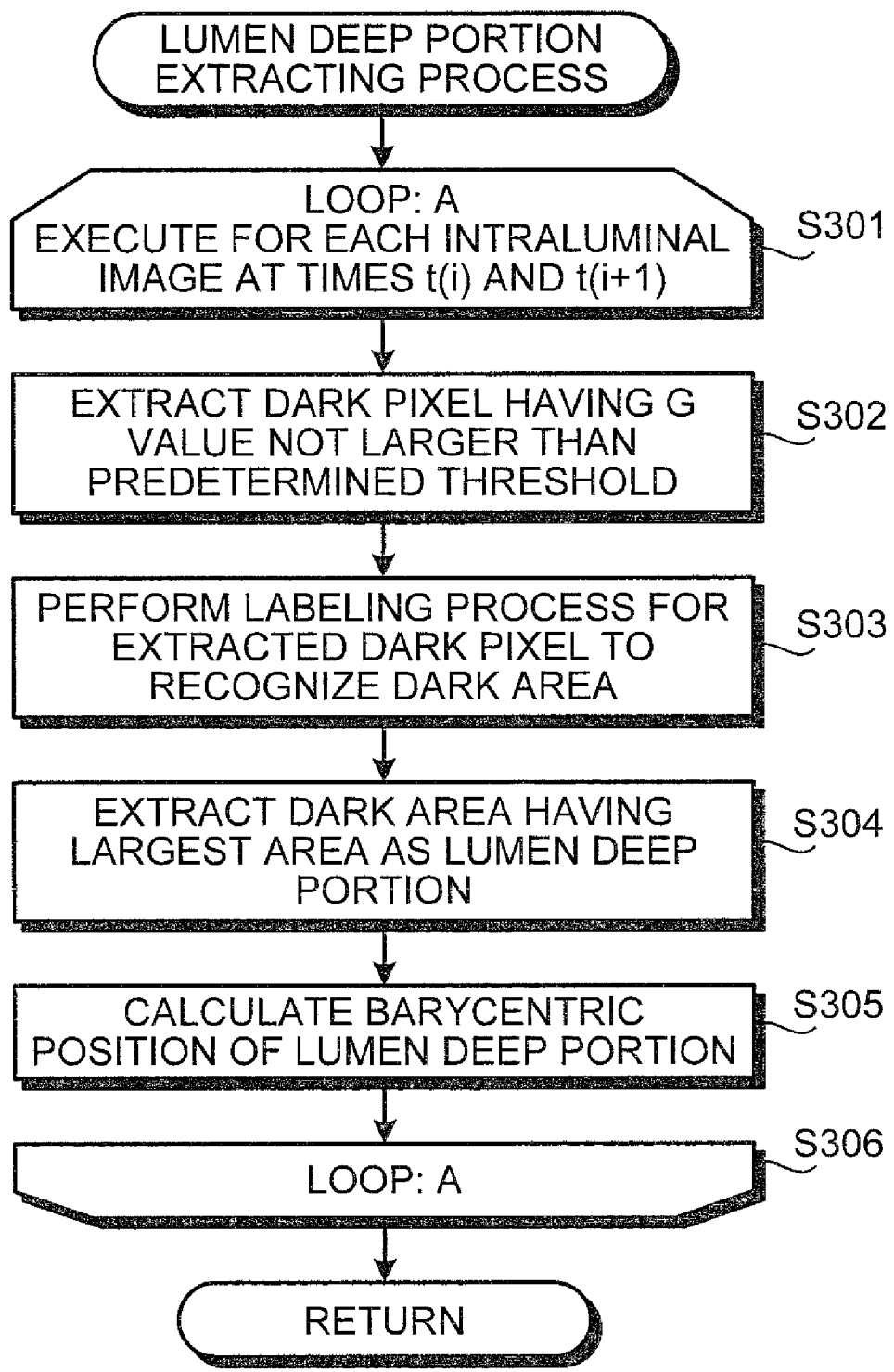
FIG. 7 is a flow chart showing a detailed procedure of a lumen deep portion extracting process.

FIG. 7 is a flow chart showing a detailed procedure of the lumen deep portion extracting process. The lumen deep portion extracting unit 13c sets the intraluminal image at the time t(i) and the intraluminal image at the time t(i+1) as the processing targets and executes processes in a loop A (step S301 to step S306). Herein, the intraluminal image, which is set as the processing target, is referred to as a "target intraluminal image" in the description of the processes in the loop A.

In the loop A, first, a G value of each pixel forming the target intraluminal image and a predetermined threshold set in advance are compared, and the pixel, of which G value is not larger than the predetermined threshold, is extracted as a dark pixel from each pixel of the target intraluminal image (step S302). Herein, the G value is used because this has a wavelength near that of an absorbing band of hemoglobin in blood and has high sensitivity and resolution, so that this well indicates light and dark information in the target intraluminal image. Incidentally, the dark pixel may be extracted using a value of the color component other than the G value. Alternately, the dark pixel may be extracted using the value indicating the light and dark information calculated using a well-known transformation technique. For example, luminance calculated by YCbCr transformation or brightness calculated by HSI transformation may be used. Also, although it is assumed to set the predetermined threshold in advance for the G value, this may be set using a well-known discrimination analysis by calculating a G value distribution of each pixel forming the target intraluminal image. As a method of the discrimination analysis, the method disclosed in "Digital Image Processing, CG-ARTS Society, 175 p, Discrimination Analysis" may be used, for example.

Subsequently, the lumen deep portion extracting unit 13c performs a well-known labeling process for the dark pixel extracted at step S302 to put a unique value (label) to a group of adjacent dark pixels (step S303). With this, the dark area in the target intraluminal image can be recognized. As a method of the labeling process, the method disclosed in "Digital Imaging Processing, CG-ARTS Society, 181 p, Labeling" may be used, for example.

Subsequently, the lumen deep portion extracting unit 13c calculates an area of each dark area in the target intraluminal image recognized at step S303, and extracts the dark area having the largest area as the lumen deep portion (step S304). Although there are the dark areas other than the lumen deep portion such as a shadow of the wrinkles of the luminal mucosal membrane in the intraluminal image, the areas are normally smaller as compared to the lumen deep portion, so that they can be differentiated from the lumen deep portion. Then, the lumen deep portion extracting unit 13c calculates the barycentric position of the dark area extracted as the lumen deep portion (step S305). Data relating to the extracted area of the lumen deep portion and the barycentric position of the lumen deep portion are associated with identification information of the target intraluminal image and held in the storage unit 12. After the lumen deep portion extracting unit 13c executes the processes in the loop A for each of the intraluminal image at the time t(i) and the intraluminal image at the time t(i+1), the procedure returns to step S105 in FIG. 2.

Figure 8:
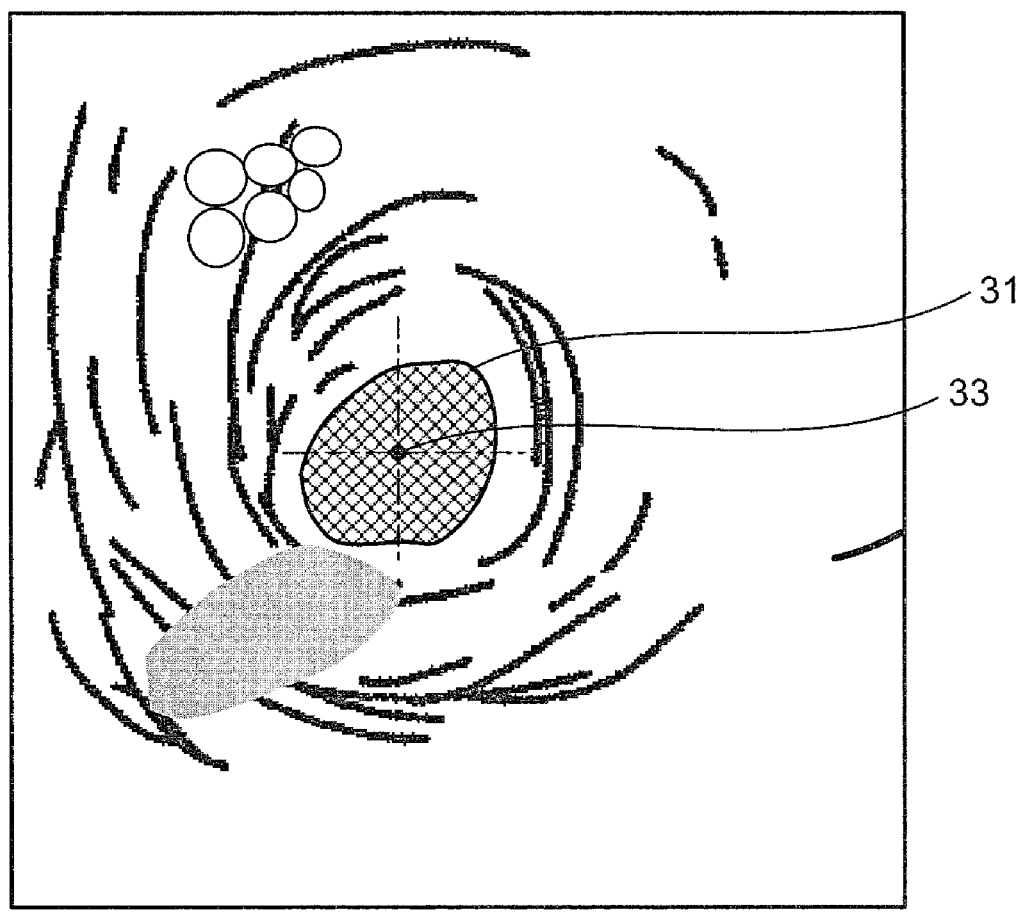
FIG. 8 is a schematic diagram showing a result of the lumen deep portion extracting process.

FIG. 8 is a schematic diagram showing a result of the lumen deep portion extracting process for the intraluminal image at the time t(i+1) illustrated in FIG. 5. In the example shown in FIG. 8, as the result of the lumen deep portion extracting process, the dark area indicated by a shaded area 31 is extracted as the lumen deep portion, and a barycentric position 33 thereof is calculated.

Next, the movement amount estimating process at step S106 in FIG. 2 is described. In the movement amount estimating process, the movement amount estimating unit 13d estimates the movement amount of the imaging device 2 from the time t(i) to the time t(i+1) based on the position of the structural area extracted by the structural area extracting unit 13a from the intraluminal image at the time t(i), the position of the corresponding area extracted by the corresponding area extracting unit 13b from the intraluminal image at the time t(i+1), and the lumen deep portion and the barycentric position thereof extracted by the lumen deep portion extracting unit 13c from the intraluminal image at the time t(i) and the intraluminal image at the time t(i+1). The estimated movement amount is stored and accumulated in the storage unit 12.

Figure 9:
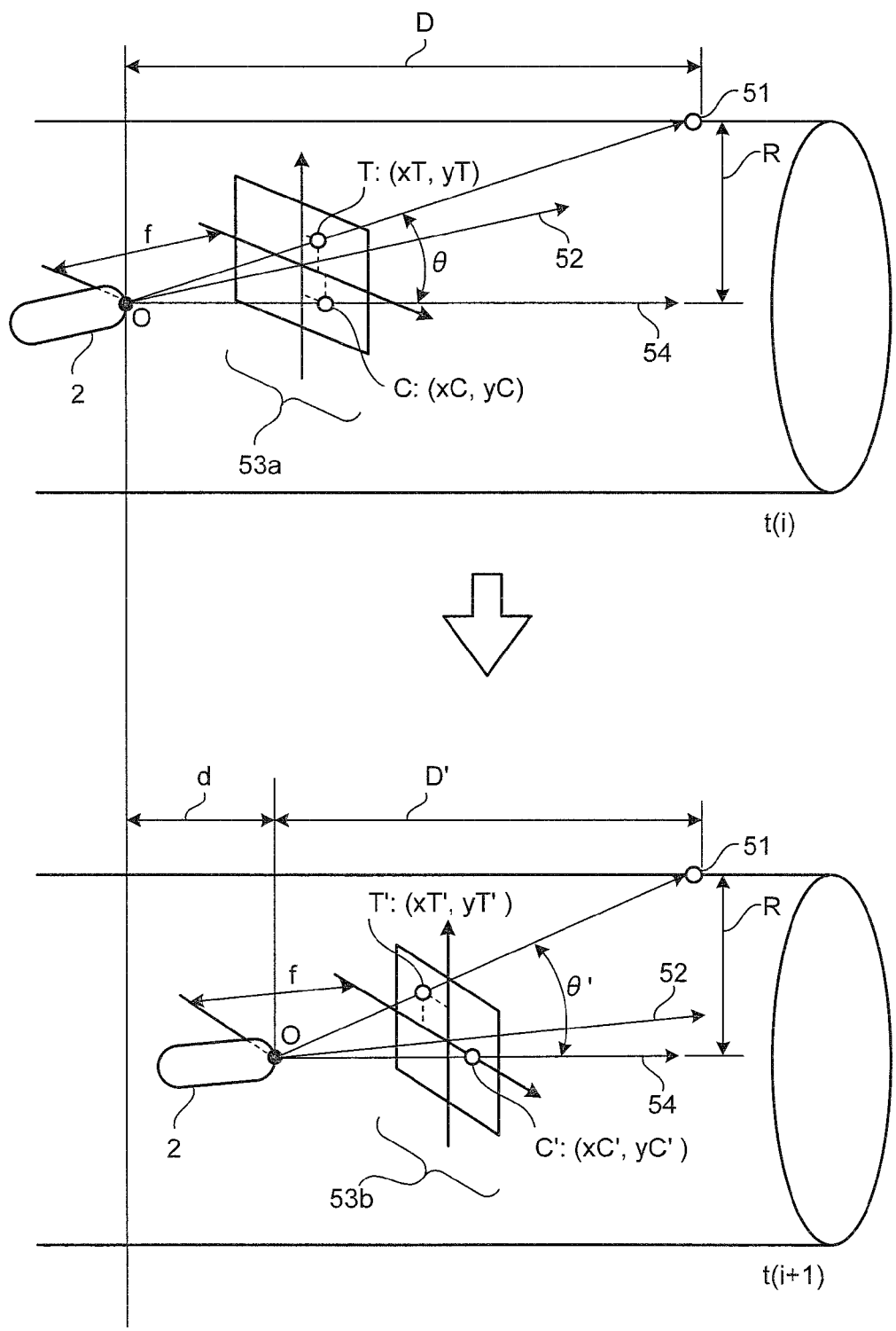
FIG. 9 is a model diagram of an inside of a lumen and of the imaging device for illustrating a movement amount estimating process.

FIG. 9 is a model diagram of an inside of the lumen and of the imaging device 2 illustrating the movement amount estimating process. A capturing situation model of the imaging device 2, which captures the intraluminal image including a feature structure 51 in the lumen at the time t(i), is shown in an upper part, and a capturing situation model of the imaging device 2, which captures the intraluminal image including the feature structure 51 at the time t(i+1), is shown in a lower part. In the capturing situation model shown in the lower part in FIG. 9, change in a capturing position (position of the imaging device 2) and change in a capturing direction relative to those of the capturing situation model shown in the upper par can be seen. Herein, a reference symbol D represents a feature structure distance obtained by projecting a distance from the imaging device 2 to the feature structure 51 on the luminal mucosal membrane at the time t(i) on an intraluminal wall surface, and a reference symbol D' represents the feature structure distance obtained by projecting the distance from the imaging device 2 to the feature structure 51 on the luminal mucosal membrane at the time t(i+1) on the intraluminal wall surface. A reference symbol O represents an optical center corresponding to a principal point of an optical system such as a lens, which the imaging device 2 has. A reference symbol R represents a luminal radius. An average luminal radius is used as the luminal radius R, for example.

Also, in the model diagram in the upper part in FIG. 9, an image coordinate 53a of the intraluminal image obtained by being projected on an imaging element of the imaging device 2 in the capturing situation model is shown. The image coordinate 53a is a coordinate system with a point of origin on a position intersecting with an optical axis 52 of the imaging device 2, and a reference symbol f represents a distance from the optical center O to the imaging element of the imaging device 2. Herein, a coordinate of a center of the structural area in which the feature structure 51 is captured in the intraluminal image obtained by the capturing situation model is set as a structural area central coordinate T (xT, yT), and a coordinate of the barycentric position in the lumen deep portion in the intraluminal image is set as a lumen deep portion barycentric coordinate C (xC, yC). Also, an angle between a vector OC from the optical center O in a direction of a barycenter of a lumen deep portion 54 and a vector OT from the optical center O to the feature structure 51 at the time t(i) is set to θ.

Similarly, in the model diagram in the lower part in FIG. 9, an image coordinate 53b of the intraluminal image obtained in the capturing situation model is shown. The image coordinate 53b is the coordinate system with the point of origin on the position intersecting with the optical axis 52 of the imaging device 2, and the reference symbol f represents the distance from the optical center O to the imaging element of the imaging device 2. Herein, a coordinate of a center of the corresponding area in which the feature structure 51 is captured in the intraluminal image obtained by the capturing situation model is set as a corresponding area central coordinate T' (xT', yT'), and a coordinate of the barycentric position of the lumen deep portion in the intraluminal image is set to a lumen deep portion barycentric coordinate C' (xC', yC'). Also, an angle between a vector OC' from the optical center O in the direction of the barycenter of the lumen deep portion 54 and a vector OT' from the optical center O to the feature structure 51 at the time t(i+1) is set to θ'.

Herein, a following equation (1) is obtained from the feature structure distance D, the structural area central coordinate T, the lumen deep portion barycentric coordinate C, the distance f and the luminal radius R of the capturing situation model in the upper part in FIG. 9. Incidentally, a reference symbol δ represents a pitch of the imaging elements of the imaging device 2. Values of each camera parameter of the distance f and the pitch δ of the imaging device are acquired in advance.

$$\frac{R}{D} = \tan\theta = \frac{\sqrt{1-\cos^2\theta}}{\cos\theta} \quad (1)$$

wherein, $$\cos\theta = \frac{\overrightarrow{OT} \cdot \overrightarrow{OC}}{|\overrightarrow{OT}| \times |\overrightarrow{OC}|}$$

$$= \frac{(xT \times \delta) \times (xC \times \delta) + (yT \times \delta) \times (yC \times \delta) + f^2}{\sqrt{(xT \times \delta)^2 \times (yT \times \delta)^2 + f^2} \times \sqrt{(xC \times \delta)^2 + (yC \times \delta)^2 + f^2}}$$

Similarly, a following equation (2) is obtained from the feature structure distance D', the structural area central coordinate T', the lumen deep portion barycentric coordinate C', the distance f and the luminal radius R of the capturing situation model in the lower part in FIG. 9.

$$\frac{R}{D'} = \frac{\sqrt{1-\cos^2\theta'}}{\cos\theta'} \quad (2)$$

wherein, $$\cos\theta' = \frac{\overrightarrow{OT'} \cdot \overrightarrow{OC'}}{|\overrightarrow{OT'}| \times |\overrightarrow{OC'}|}$$

$$= \frac{(xT' \times \delta) \times (xC' \times \delta) + (yT' \times \delta) \times (yC' \times \delta) + f^2}{\sqrt{(xT' \times \delta)^2 \times (yT' \times \delta)^2 + f^2} \times \sqrt{(xC' \times \delta)^2 + (yC' \times \delta)^2 + f^2}}$$

Then, a following equation (3) is obtained from equations (1) and (2).

$$\frac{R}{D} - \frac{R}{D'} = \frac{\sqrt{1-\cos^2\theta}}{\cos\theta} - \frac{\sqrt{1-\cos^2\theta'}}{\cos\theta'} \quad (3)$$

A following equation (4) is obtained by modifying equation (3).

$$D - D' = \left( \frac{\cos\theta}{\sqrt{1-\cos^2\theta}} - \frac{\cos\theta'}{\sqrt{1-\cos^2\theta'}} \right) \times R \quad (4)$$

D-D' in equation (4) represents a difference in the feature structure distances obtained by projecting the distances from the imaging device 2 to the feature structure 51 on the luminal mucosal membrane at the time t(i) and the time t(i+1) on the intraluminal wall surface, and this corresponds to a movement amount d of the imaging device 2 from the time t(i) to the time t(i+1) shown in the lower part in FIG. 9. By obtaining D-D' in this manner, the movement amount of the imaging device 2 from the time t(i) to the time t(i+1) can be estimated. Specifically, the movement amount estimating unit 13d obtains D-D' for each feature structure corresponding to each structural area extracted by the structural area extracting process. Then, the movement amount estimating unit 13d calculates an average value of a plurality of obtained values of the movement amount to estimate the movement amount of the imaging device 2 from the time t(i) to the time t(i+1).

Next, the position estimating process at step S109 in FIG. 2 is described. In the position estimating process, the position estimating unit 13e obtains an accumulated value of the movement amounts of the imaging device 2 from the time t(i) to the time t(i+1) estimated as the result of the movement amount estimating process and is accumulated in the storage unit 12 to estimate the position of the imaging device 2 at each time when capturing each intraluminal image. The accumulated value corresponds to the movement distance of the imaging device 2 from the time t(0) at the entrance of the lumen to the time t(T) at the exit of the lumen. Incidentally, a relative position of the imaging device 2 in the lumen at each time may be determined by dividing the obtained accumulated value by a sum total of the movement amounts of the imaging device 2, which moves from the entrance to the exit of the lumen, i.e., an entire length of the lumen.

Figure 10:
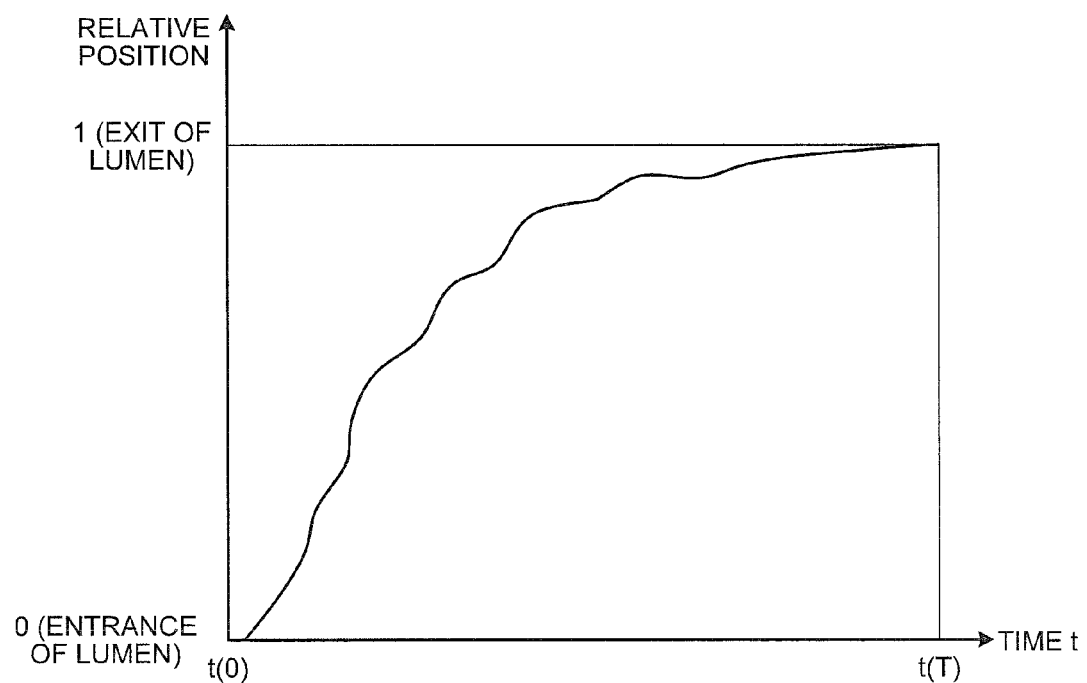
FIG. 10 is a schematic diagram showing a result of a position estimating process.

FIG. 10 is a schematic diagram showing a result of the position estimating process, which indicates a time-series change of an estimated relative position of the imaging device 2 in which an abscissa axis and a longitudinal axis represent the time t and the relative position of the imaging device 2 from the entrance to the exit of the lumen, respectively. With this, it is possible to know the relative position of the imaging device 2 in the lumen from the entrance or the exit of the lumen at each time when capturing the intraluminal image based on the capturing time of the intraluminal image in which a diseased site is captured, and it becomes possible to estimate the position of the diseased site.

In this manner, in the first embodiment, by processing the intraluminal images captured in time series by the imaging device 2, the movement amount of the imaging device 2 can be estimated with a simple configuration, and the position of the imaging device 2 in the lumen at each time when capturing each intraluminal image can be estimated without providing a separate device in the imaging device or outside the body of a patient. As a result, the imaging device does not become large and a system configuration is not complicated unlike in the case in which a device such as a single-core coil for measuring the movement amount is separately incorporated in the imaging device. Thus the compact imaging device and a compact extracorporeal device can be manufactured with lower costs.

Incidentally, the position of the imaging device 2 at the time when the imaging device 2 captures the diseased site is in the vicinity of the diseased site and is not perfectly identical to the position of the diseased site. However, it is not required to strictly grasp the position of the diseased site when determining whether an insert root at the time of insertion of a medical treatment tool into the lumen of the patient should be oral or transluminal or when determining whether a position of the body of the patient to be cut should be near an upper portion or a lower portion of a specific organ, by utilizing the intraluminal image in which the diseased site is captured. In this case, when information of a rough position of the diseased site is obtained by the first embodiment, the information of the position can be used in a medical treatment thereafter such as tissue collection, arrest of breading and resection of the diseased site.

Also, although it is described in the first embodiment that the target is from the entrance to the exit of the lumen, it is also possible to estimate the position of the imaging device 2 by setting a starting position or an ending position of the specific organ, such as the small intestine and the large intestine, as a base point. With this, it is possible to acquire the information about how far the position of the diseased site is from the starting position or the ending position of the specific organ along the lumen.

Also, although the structural area is extracted earlier than the lumen deep portion in the first embodiment, it is possible to extract the lumen deep portion first and then extract the structural area based on the position of the lumen deep portion. For example, it is possible to extract the structural area so as to circle the lumen deep portion.

Also, although the method of extracting a plurality of areas suitable as the structural areas while scanning the rectangular area of the predetermined size is shown in the first embodiment, the shape of the structural areas is not required to be rectangle and may be an arbitrary shape. For example, it is possible to determine for each pixel in the rectangular area whether the pixel is the pixel of the luminal mucosal membrane so as to extract an area of an arbitrary shape, which is obtained by removing the pixels determined not to be the pixels of the luminal mucosal membrane, as the structural area.

Also, it is possible to divide the intraluminal image into a reticular pattern of a predetermined size in advance, perform steps S202 to S205 shown in FIG. 4 for each divided area, and finally extract a predetermined number of divided areas as the structural areas in the descending order of the broadness of distribution area, and as a result, the load of calculation to extract the structural area can be reduced. Herein, when only one structural area is extracted instead of extracting a plurality of structural areas is, the load of calculation can be further reduced.

Second Embodiment

Figure 11:
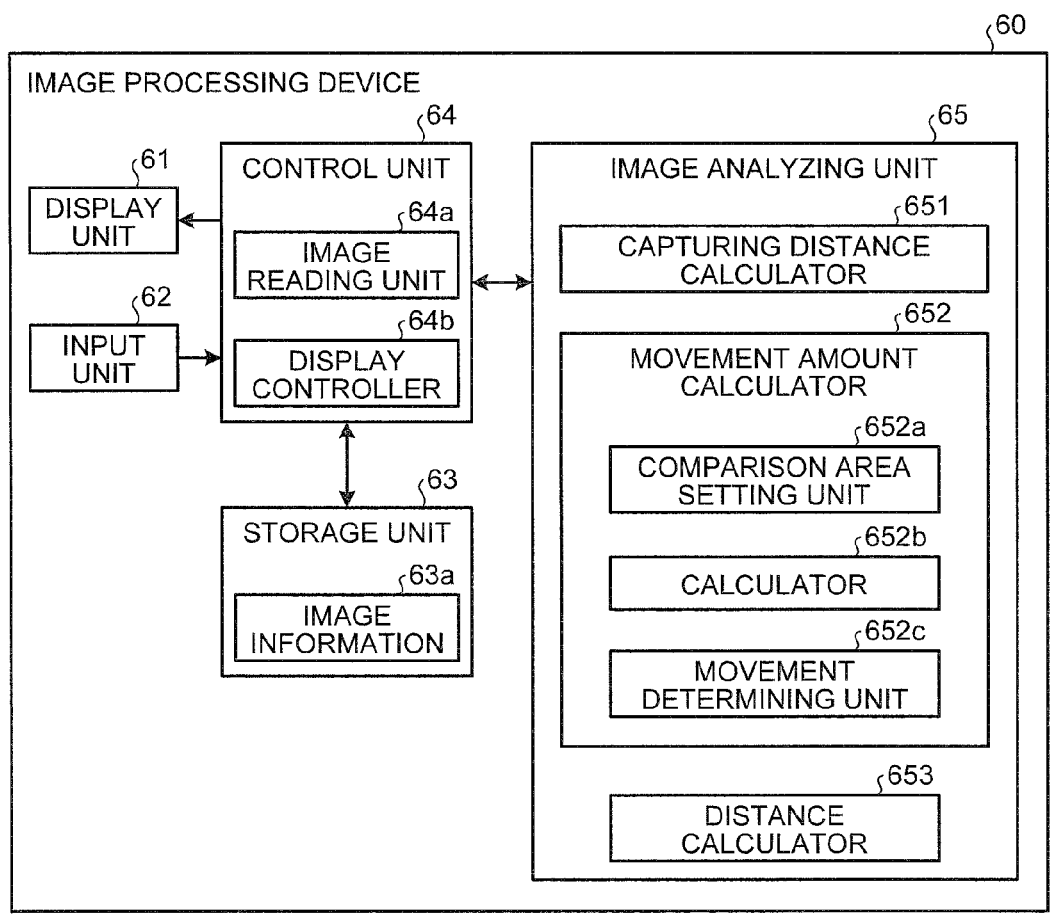
FIG. 11 is a block diagram showing a configuration of an image processing device according to a second embodiment.

Next, an image processing device according to an embodiment of the present invention is described. FIG. 11 is a block diagram of the image processing device according to a second embodiment of the present invention. As shown in FIG. 11, an image processing device 60 is provided with a display unit 61 for outputting various pieces of information, an input unit 62 for accepting an input of the various pieces of information, a storage unit 63 for storing the various pieces of information, a control unit 64 for controlling process and operation of each unit of the image processing device 60 and an image analyzing unit 65 for analyzing the image information. The display unit 61, the input unit 62, the storage unit 63, the control unit 64 and the image analyzing unit 65 are electrically connected to each other.

The display unit 61 is provided with a liquid crystal display and the like to display the various pieces of information including the image. Specifically, the display unit 61 displays the image stored in the storage unit 63 and a graphical user interface (GUI) screen to ask a user of the image processing device 60 to input various pieces of processing information.

The input unit 62 accepts the input of the image to be processed by the image processing device 60 and the various pieces of processing information. Specifically, the input unit 62 is provided with a communication interface such as USB and IEEE 1394 to accept the input of the image from an external device. Also, the input unit 62 is provided with various switches, an input key, a mouse, a touch panel and the like, and accepts a designation of an area in the image, in which an area of interest i.e. an object is captured of which distance from a predetermined position the user desires to grasp. Incidentally, the input unit 62 is provided with an interface corresponding to the portable recording medium such as the various memory cards, the CD and the DVD, and may accept the input of the image from the portable recording medium.

The storage unit 63 is constructed by a ROM storing the various processing programs in advance, and a RAM storing process parameters, process data and the like of each process. The storage unit 63 stores image information 63a of a row of images captured in time series by a moving imaging device. Incidentally, the storage unit 63 may be provided with the portable recording medium such as the various memory cards, the CD and the DVD as a detachable image storage unit.

The control unit 64 is constructed by the CPU and the like, which executes the various processing programs stored in the storage unit 63. Specifically, the control unit 64 is provided with an image reading unit 64a and a display controller 64b. The image reading unit 64a reads the image information stored in the storage unit 63. Also, the display controller 64b controls to display the image read by the image reading unit 64a and the like on the display unit 61.

The image analyzing unit 65 is provided with a capturing distance calculator 651, a movement amount calculator 652 and a distance calculator 653. The capturing distance calculator 651 analyzes the image, in which the area of interest is captured, to calculate the capturing distance between the area of interest and the imaging device. Also, the movement amount calculator 652 analyzes the images forming the row of time-series captured images to calculate the movement amount of the imaging device, which moves during capturing each image. Further, the distance calculator 653 accumulates the movement amounts calculated by the movement amount calculator 652 and calculates the accumulated movement amount after the imaging device leaves the predetermined position. Incidentally, the predetermined position is a position of a predetermined reference point in a tract, or the position at which the imaging device first captures the image, or the position specified by the user through the input unit 62.

Further, the movement amount calculator 652 is provided with a comparison area setting unit 652a, a calculator 652b and a movement determining unit 652c. The comparison area setting unit 652a sets a comparison area in each image. The comparison area is an area having a feature with which the area can be distinguished from another area on the image, and is the area showing a characteristic frequency distribution when Fourier transforming each image into a frequency space, for example. Other than this, an area, which can be effectively used when performing the template matching because the area itself is characteristic, can be set as the comparison area. For example, an area recognized as the characteristic area when performing area division or an area set by the user in the image can be set as the comparison area.

The calculator 652b calculates the movement amount of the imaging device between the captures of two or more continuous images based on positional displacement between the comparison areas set in the images. Herein, the calculator 652b calculates positional displacement between the comparison areas using the template matching. That is, the calculator 652b sets the comparison area set by the comparison area setting unit 652a as the template, detects an area having the strongest correlation with the template in another image, detects the positional displacement on the image area between the comparison area and the area having the strongest correlation with the comparison area, and calculates the movement amount of the imaging device based on the positional displacement.

Incidentally, the calculator 652b may detect the positional displacement of the object between the images by setting an entire image area as the template. In this case, the comparison area setting unit 652a is not required.

Also, the movement determining unit 652c compares the two or more continuous images to determine whether the imaging device moves between the captures of the images. When the movement determining unit 652c determines that the imaging device moves between the captures of the images, the calculator 652b performs the calculation process of the movement amount between the images.

Figure 12:
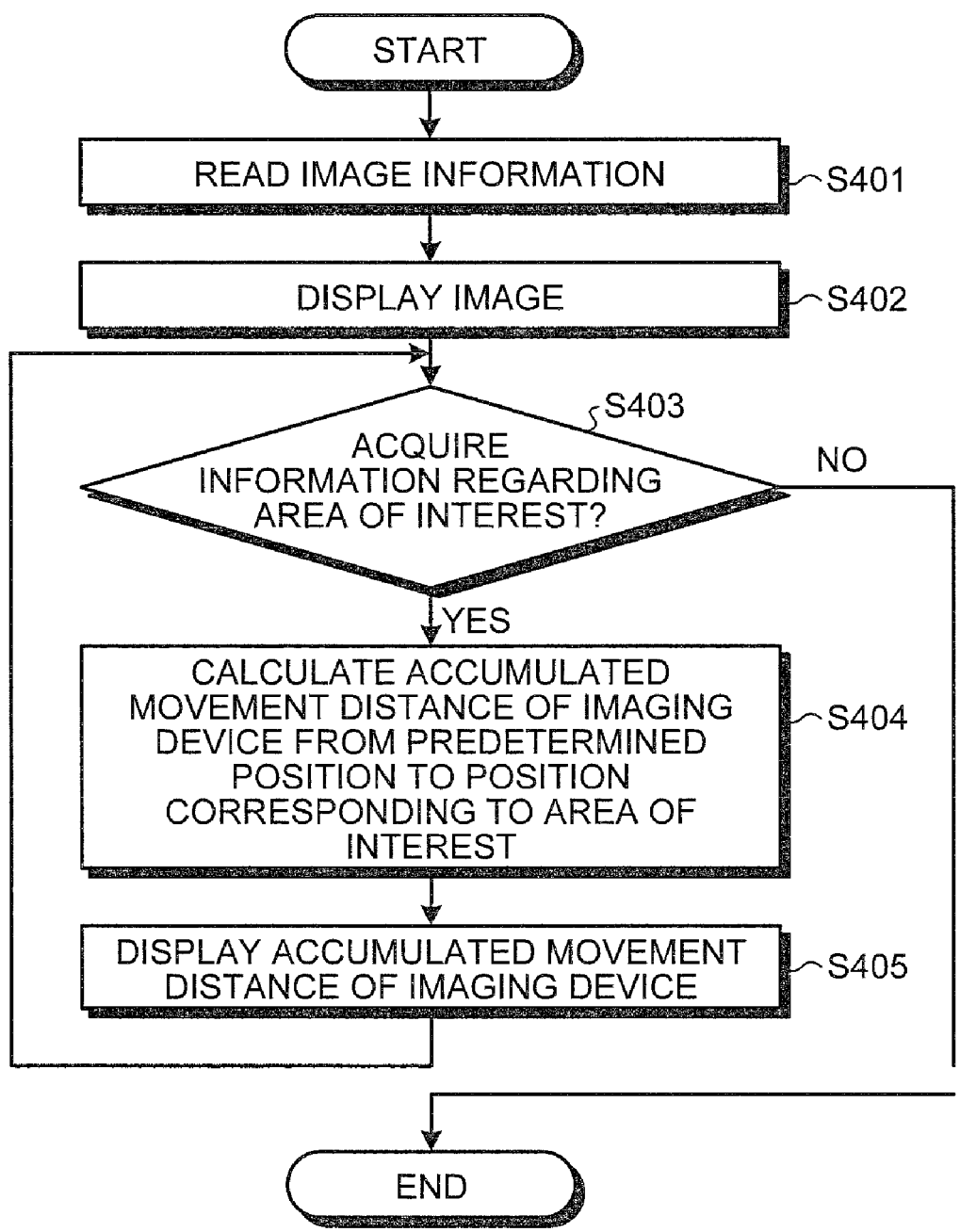
FIG. 12 is a flow chart showing an overview of an image analyzing process performed by the image processing device shown in FIG. 11.

Next, a procedure of the image analyzing process performed by the image processing device 60 is described. FIG. 12 is a flow chart showing a procedure in which the image processing device 60 calculates to display the accumulated movement amount after the imaging device leaves the predetermined position, that is, the accumulated movement distance of the imaging device under the control of the control unit 64. As shown in FIG. 12, first, the image reading unit 64a reads the image information 63a stored in the storage unit 63 (step S401), and the display controller 64b displays the read image on the display unit 61 (step S402). Thereafter, the control unit 64 accepts the input of the area of interest from the user through the input unit 62 (step S403). Incidentally, although it is assumed to accept the designation of the area in the image, in which the area of interest is captured, from the user in the second embodiment, the process at step S403 may be such that the area of interest in the image is automatically extracted. For example, the area of interest in the image may be set (extracted) by preparing in advance image feature (such as color and texture) of the area, which is desired to be extracted as the area of interest, and extracting the area provided with the image feature by the well-known method such as the template matching and the pattern recognition. When the control unit 64 acquires the information regarding the area of interest (step S403: Yes), the control unit controls the image analyzing unit 65 to calculate the accumulated movement distance of the imaging device from the predetermined position to the position corresponding to the area of interest (step S404). Thereafter, the display controller 64b causes the display unit 61 to display the calculated accumulated movement distance (step S405). Incidentally, when the control unit 64 does not acquire the information regarding the area of interest (step S403: No), the control unit 64 terminates the image analyzing process.

Figure 13:
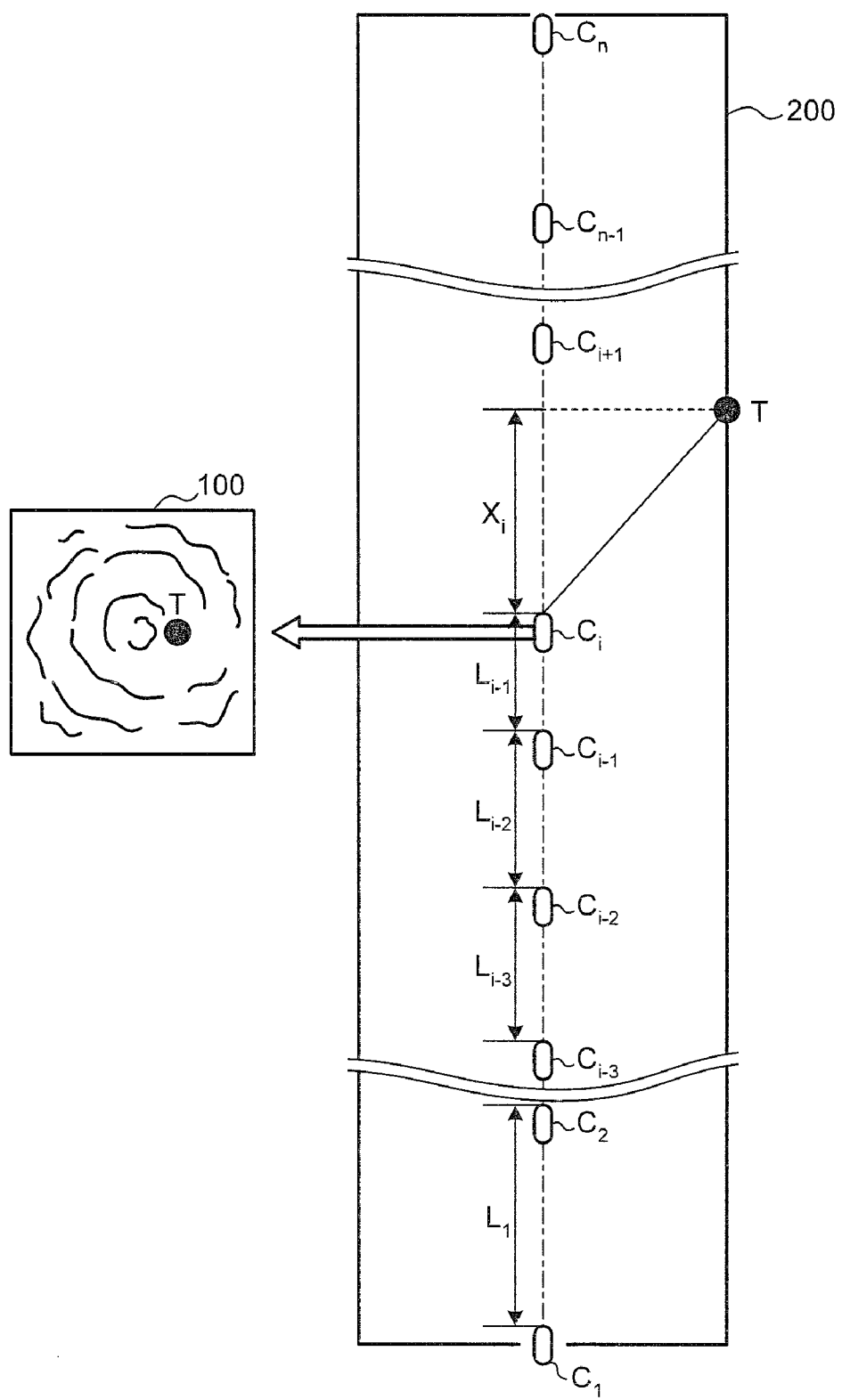
FIG. 13 is a view showing a movement trajectory of an imaging device in a tract and an image captured by the imaging device.

Herein, the process performed by the image analyzing unit 65 at step S404 is described. FIG. 13 is a view showing an image 100 in which an area of interest T is captured and capturing positions $C_1$-$C_i$-$C_n$ of the area of interest T and each image in a tract 200. As shown in FIG. 13, after the imaging device leaves the capturing position $C_1$ being a starting point, the imaging device captures the images at the capturing positions $C_1$-$C_i$-$C_n$ while moving on a tract axis of the tract 200 in a direction of the tract axis. Incidentally, the image 100 is the image captured at the capturing position $C_i$.

A case in which the user browses the image displayed on the display unit 61 and instructs to the control unit 64 to calculate the accumulated movement distance of the imaging device from the starting point (capturing position $C_i$) to the position corresponding to the area of interest T is described. In this case, the image analyzing unit 65 calculates the accumulated movement distance of the imaging device by adding the distances between each capturing position, that is, the accumulated amount of movement amounts $L_1$ to $L_{i-1}$ of the imaging device from each capturing position to a next capturing position, and a capturing distance $X_i$ between the capturing position $C_i$ and the area of interest T in the direction of the tract axis as shown in FIG. 13.

Specifically, the capturing distance calculator 651 analyzes the image 100 to calculate the capturing distance $X_i$. Also, the movement amount calculator 652 analyzes the images captured at the capturing positions $C_1$ to $C_i$ to calculate the movement amounts $L_1$ to $L_{i-1}$ of the imaging device. Thereafter, the distance calculator 653 accumulates and adds the movement amounts $L_1$ to $L_{i-1}$ and further adds the capturing distance $X_i$ to the accumulated amount, thereby calculating the accumulated movement distance of the imaging device from the capturing position $C_1$ being the starting point to the position corresponding to the area of interest T. Incidentally, it is possible that the movement amount, which does not satisfy a condition determined by a predetermined threshold, is not set as the target of the accumulation addition, and only the movement amount, which satisfies the condition determined by the predetermined threshold, is set as the target of the accumulation addition. For example, the movement amount smaller than the predetermined threshold may be removed from the target of the accumulation addition, or the movement amount not smaller than the predetermined threshold may be removed from the target of the accumulation addition.

Figure 14:
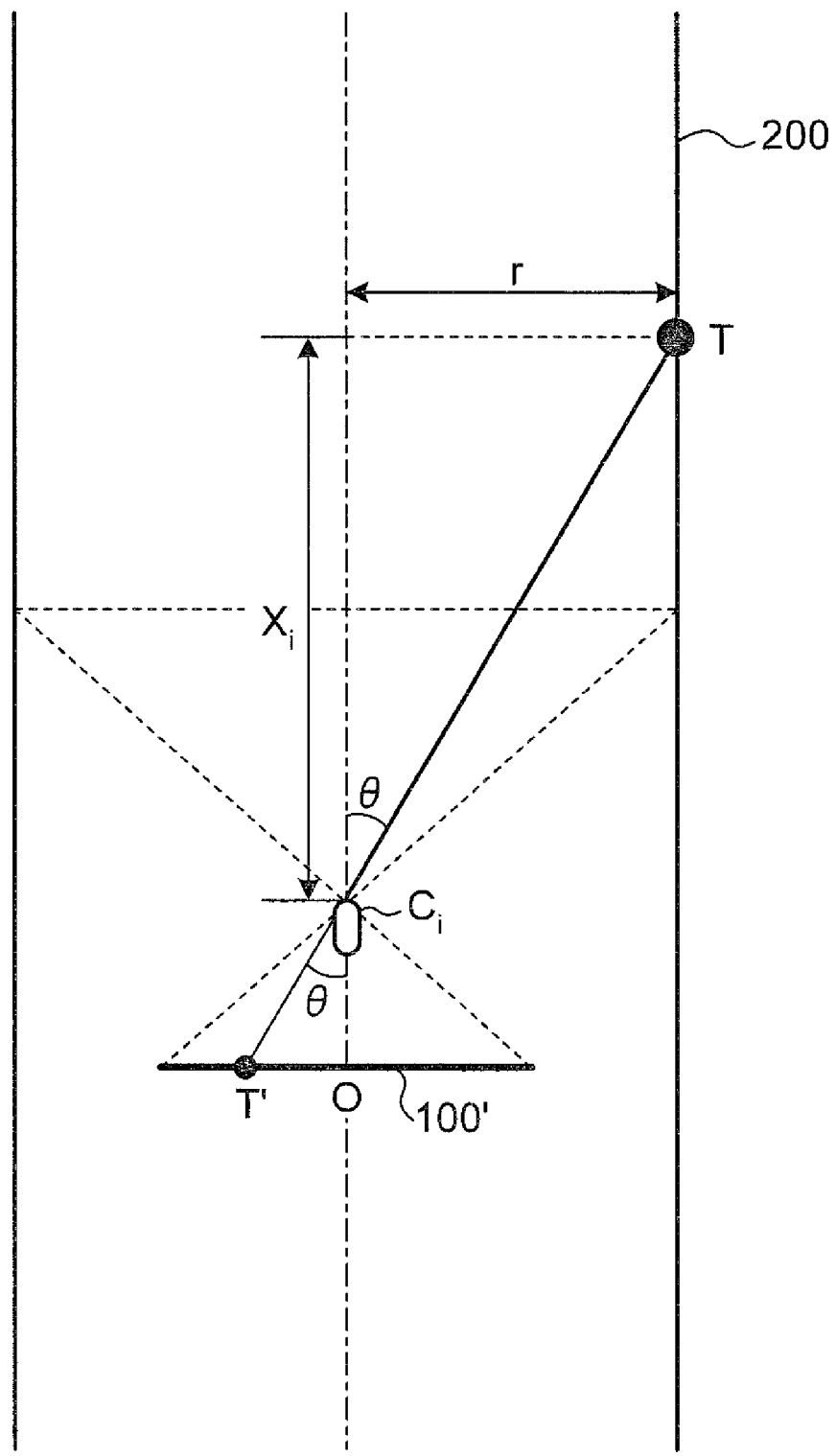
FIG. 14 is a view illustrating an overview of a method for calculating a capturing distance.

Herein, the image analyzing process performed by the capturing distance calculator 651 and the movement amount calculator 652 is described. First, the image analyzing process performed by the capturing distance calculator 651 is described with reference to FIG. 14. FIG. 14 is a view showing positional relationship between the capturing position $C_i$ and the area of interest T in the tract 200, and positional relationship between the area of interest T' and a focal point O on an imaging plane 100' of the imaging device obtained by capturing the image 100. Incidentally, it is assumed that the imaging device moves on the tract axis in the direction of the tract axis, and an optical axis of the imaging device and the tract axis conforms to each other. As shown in FIG. 14, when an intersecting angle between a line connecting the imaging device and the area of interest T and the tract axis (optical axis) is set to θ, relationship between a tract radius r of the tract 200 and the capturing distance $X_i$, and relationship between a distance OT' between the focal point O and the area of interest T' and a focal distance a are represented as follows.

$$\tan\theta = \frac{r}{X_i} = \frac{OT'}{a} \quad (5)$$

$$X_i = \frac{ra}{OT'} \quad (6)$$

In the second embodiment, it is assumed that the tract radius r is known, and the focal distance a is information included in the image information 63a as a capturing condition of the imaging device. Therefore, the capturing distance calculator 651 calculates the capturing distance $X_i$ using equation (6) and the information such as the distance OT' obtained by analyzing the image 100. Incidentally, although the tract radius r is known in the second embodiment, the tract radius r may be calculated by analyzing the image 100.

Figure 15:
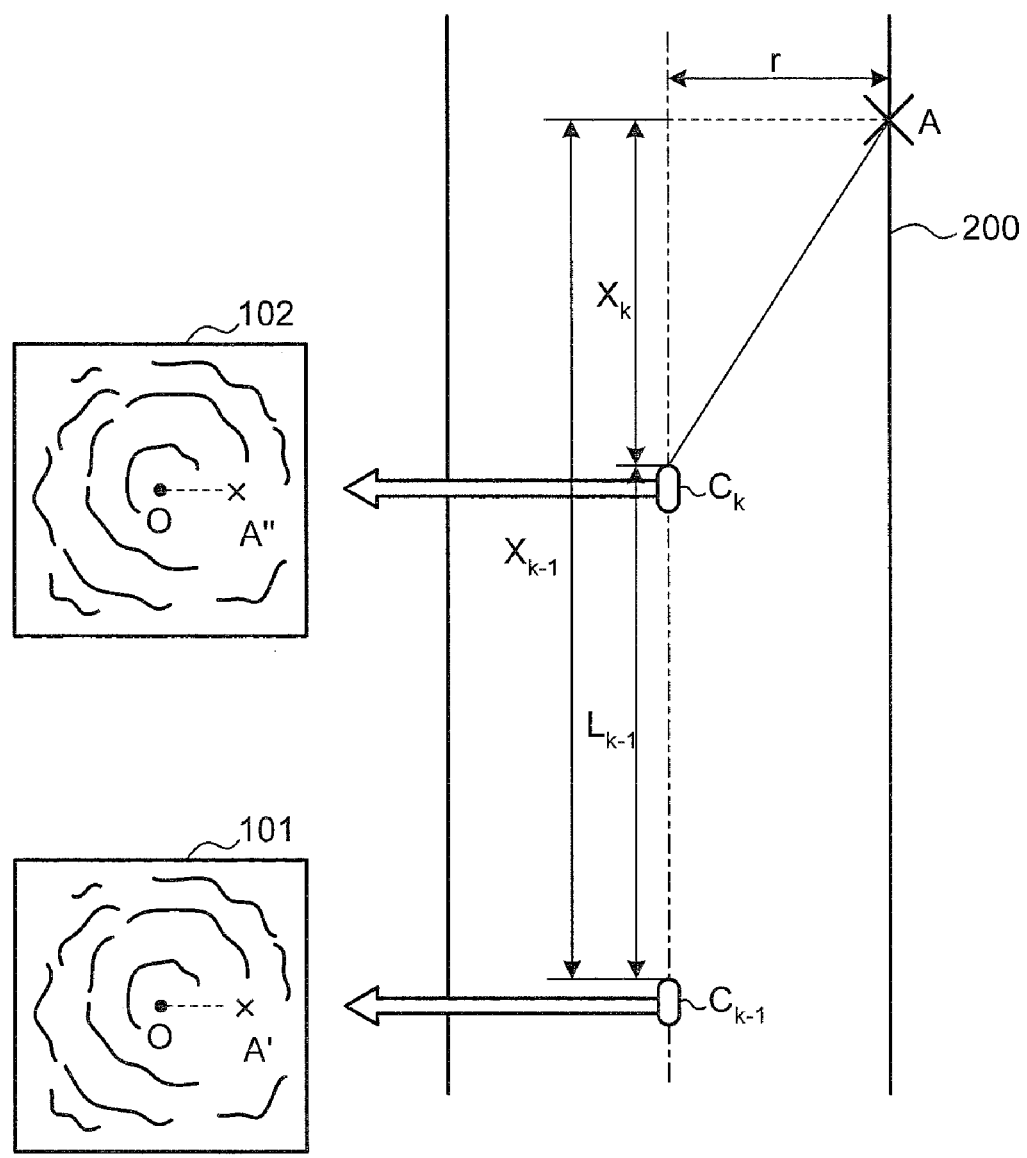
FIG. 15 is a view illustrating an overview of a method for calculating a movement amount of the imaging device.

Next, the image analyzing process performed by each part of the movement amount calculator 652 is described with reference to FIG. 15. FIG. 15 is a view showing positional relationship between a comparison area A set by the comparison area setting unit 652a and capturing positions $C_{k-1}$ and $C_k$ at which the comparison area A is captured, and images 101 and 102 captured at the capturing positions $C_{k-1}$ and $C_k$. Incidentally, in FIG. 15, the comparison area A on the images 101 and 102 are set as comparison areas A' and A". As shown in FIG. 15, a movement amount $L_{k-1}$ of the imaging device from the capturing position $C_{k-1}$ to the capturing position $C_k$ can be calculated as a difference between a capturing distance $X_{k-1}$, which is a distance between the capturing position $C_{k-1}$ and the comparison area A in the direction of the tract axis, and a capturing distance $X_k$, which is a distance between the capturing position $C_k$ and the comparison area A in the direction of the tract axis. Since the capturing distances $X_{k-1}$ and $X_k$ can be calculated using equation (6), the movement amount is represented as a following equation (7).

$$L_{k-1} = X_{k-1} - X_k = rd\left(\frac{1}{OA'} - \frac{1}{OA''}\right) \qquad (7)$$

Therefore, the comparison area setting unit 652a sets the comparison area A in the images 101 and 102, and the calculator 652b calculates the movement amount $L_{k-1}$ using equation (7) and distances OA' and OA'' obtained by analyzing the images 101 and 102. The comparison area setting unit 652a and the calculator 652b similarly calculate the movement amounts $L_1$ to $L_{i-1}$ of the imaging device between each capturing position of the capturing positions $C_1$ to $C_i$.

Figure 16:
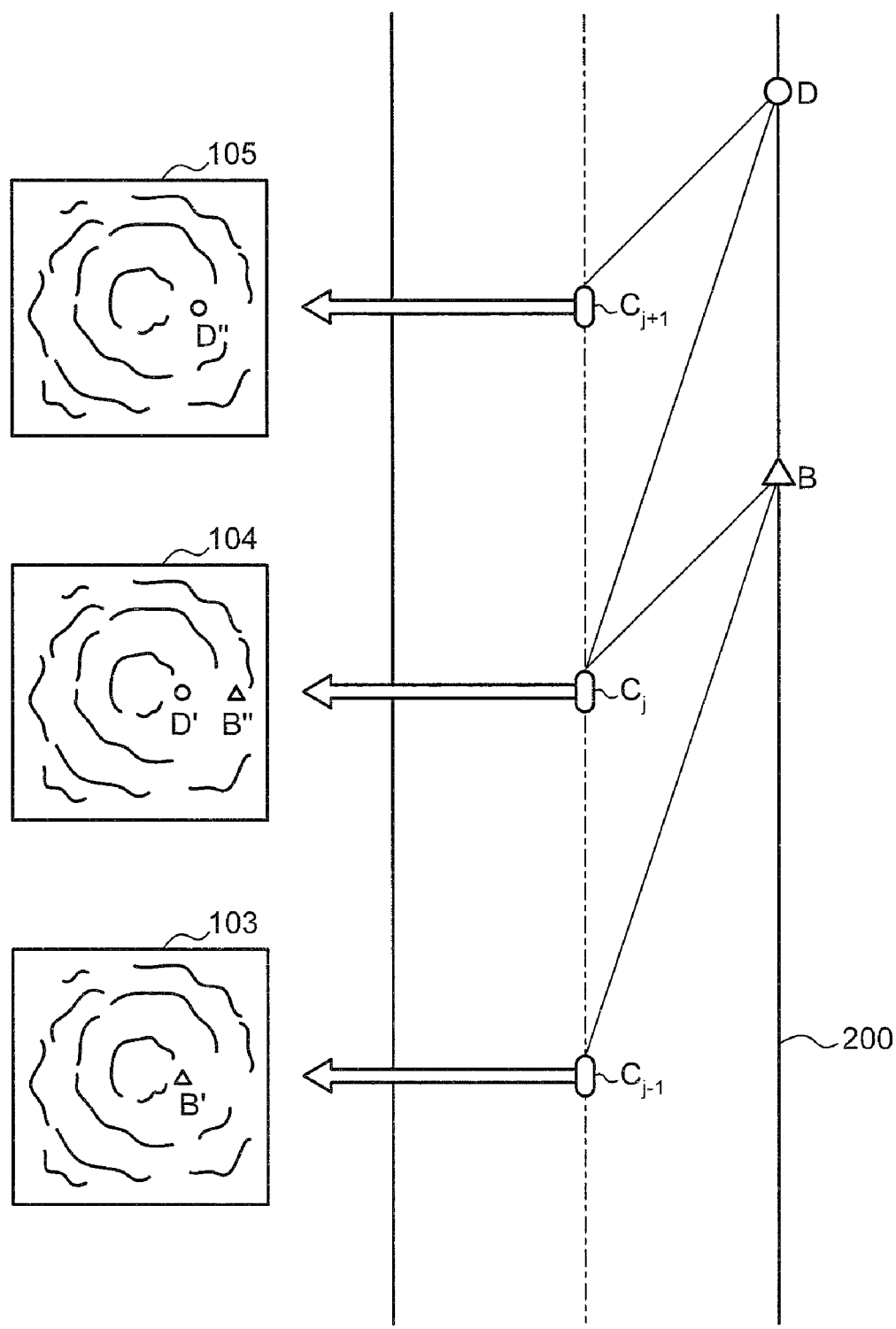
FIG. 16 is a view showing an example of comparison area setting.

Incidentally, the comparison area setting unit 652a always sets one or more comparison area on each image. Further, the comparison area setting unit 652a sets another comparison area D before a predetermined comparison area B frames out as shown in FIG. 16. The comparison areas are set in this manner in order to calculate the movement amounts of the imaging device between all the capturing positions.

Figure 17:
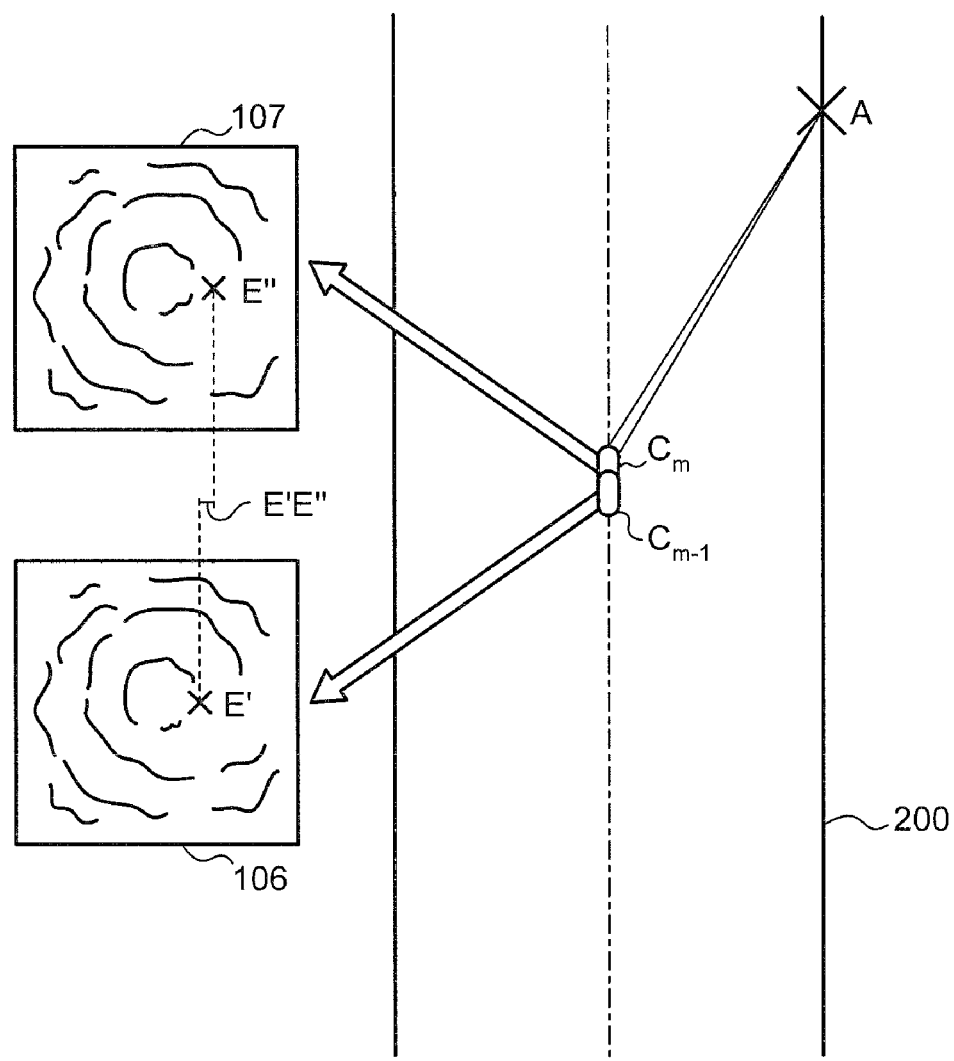
FIG. 17 is a view showing images and capturing positions in a case in which it is determined that the imaging device has not moved.

Also, when a positional displacement amount between the comparison areas on the image is smaller than the predetermined threshold between the continuous images, the movement determining unit 652c determines that the imaging device does not move between the captures of the images. For example, as shown in FIG. 17, when a positional displacement amount E'E'' between the comparison areas E' and E'' on images 106 and 107 captured at capturing positions $C_{m-1}$ and $C_m$ is smaller than the predetermined amount, it is determined that the imaging device does not move between the capturing positions $C_{m-1}$ and $C_m$, and the movement amount is calculated when this is not smaller than the predetermined threshold.

In this manner, the image processing device 60 according to the second embodiment calculates the movement amount of the imaging device between each image and calculates the capturing distance from the imaging device, based on the positional displacement between the comparison areas on the images forming the row of images captured in time series by the moving imaging device. Therefore, according to the image processing device 60, information indicating a degree of movement of the imaging device when each image is captured becomes clear, and it is possible to grasp the accumulated movement distance of the imaging device between the predetermined position and the position corresponding to the area of interest.

Incidentally, in the above-described second embodiment, when a tract length being the distance between the predetermined positions in the direction of the tract axis is known, the movement amount of the imaging device can be corrected using the tract length. That is, it is possible to normalize the accumulated movement amount of the imaging device between the predetermined positions calculated by analyzing the image information 63a by the known tract length to correct the calculated accumulated movement amount. The accumulated movement distance can be calculated more correctly by calculating the movement distance of the imaging device between the predetermined position and the position corresponding to the area of interest using the corrected accumulated movement amount.

Also, when setting a plurality of comparison areas between each image, the movement amount is calculated by performing a following process, for example.

In this case, the calculator 652b calculates the movement amount of the imaging device between the images for each area of divided areas $F_{11}$ to $F_{NM}$ obtained by dividing an entire image area into M×N, as shown in FIG. 18, for example. Herein, the movement amount of the imaging device calculated for each divided area is referred to as an area movement amount. The movement amount of the imaging device between predetermined images is calculated using the area movement amount. For example, the calculator 652b calculates the movement amount between each image by applying a statistical process to the area movement amount. For example, an average value of a plurality of area movement amounts is regarded as the movement amount between each image. Alternatively, the average value of the area movement amounts within a predetermined threshold range of each area movement amount is regarded as the movement amount between each image.

Third Embodiment

In the above-described second embodiment, the distance obtained by adding the movement amount of the imaging device from the predetermined position to the position at which the area of interest is captured and the capturing distance between the imaging device, which captures the area of interest, and the area of interest is calculated as the accumulated movement distance that is a movement distance of the imaging device from the predetermined position. In a third embodiment, the movement amount of the imaging device from the predetermined position to the position at which the area of interest is captured is calculated as the accumulated movement distance that is the movement distance of the imaging device from the predetermined position. This is based on the fact that when the movement amount of the imaging device is extremely larger as compared to the capturing distance, the accumulated value of the movement amounts of the imaging device can be approximated to the distance from the predetermined position to the position corresponding to the area of interest.

Figure 19:
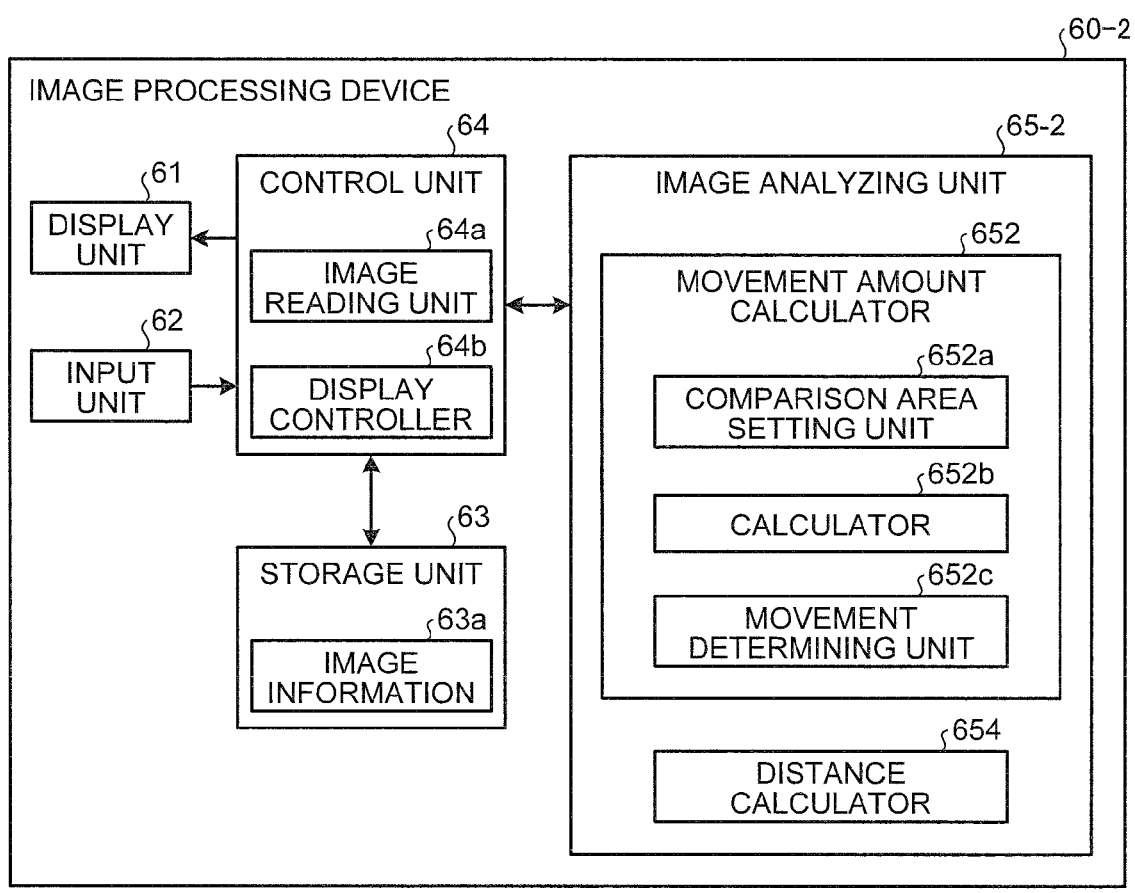
FIG. 19 is a block diagram showing a configuration of an image processing device according to a third embodiment of the present invention.

That is, as shown in FIG. 19, an image processing device 60-2 according to the third embodiment is provided with an image analyzing unit 65-2 in place of the image analyzing unit 65 provided on the image processing device 60. Also, the image analyzing unit 65-2 is provided with the movement amount calculator 652 provided on the image analyzing unit 65, and a distance calculator 654 in place of the distance calculator 653. The image processing device 60-2 is not provided with the capturing distance calculator 651. Other configuration is the same as that of the image processing device 60.

The distance calculator 654 accumulates and adds the movement amounts of the imaging device calculated by the movement amount calculator 652 to calculate the accumulated movement distance of the imaging device from the predetermined position to the position corresponding to the area of interest. Incidentally, the procedure of the image analyzing process performed by the image processing device 60-2 in order to calculate the accumulated movement distance of the imaging device is similar to the image processing procedure performed by the image processing device 60 shown in FIG. 12. However, it is not required to calculate the capturing distance between the area of interest and the imaging device in this embodiment, so that it is not required to specify the position of the area of interest in the image as in step S403 of the second embodiment. In this embodiment, the image in which the area of interest is captured may be designation input by the user or may be automatically specified in place of step S403.

In this manner, the accumulated movement distance of the imaging device between the predetermined position and the position corresponding to the area of interest is calculated by approximating the same to the movement amount of the imaging device from the predetermined position to the position at which the area of interest is captured in the third embodiment. Therefore, a calculation process amount is reduced as compared to the second embodiment, and a load of the calculation process of the image processing device is reduced.

Fourth Embodiment

Next, a fourth embodiment of the present invention is described. In the fourth embodiment, the image area in which the comparison area is set is limited in the image processing device according to the second or third embodiment.

Figure 20:
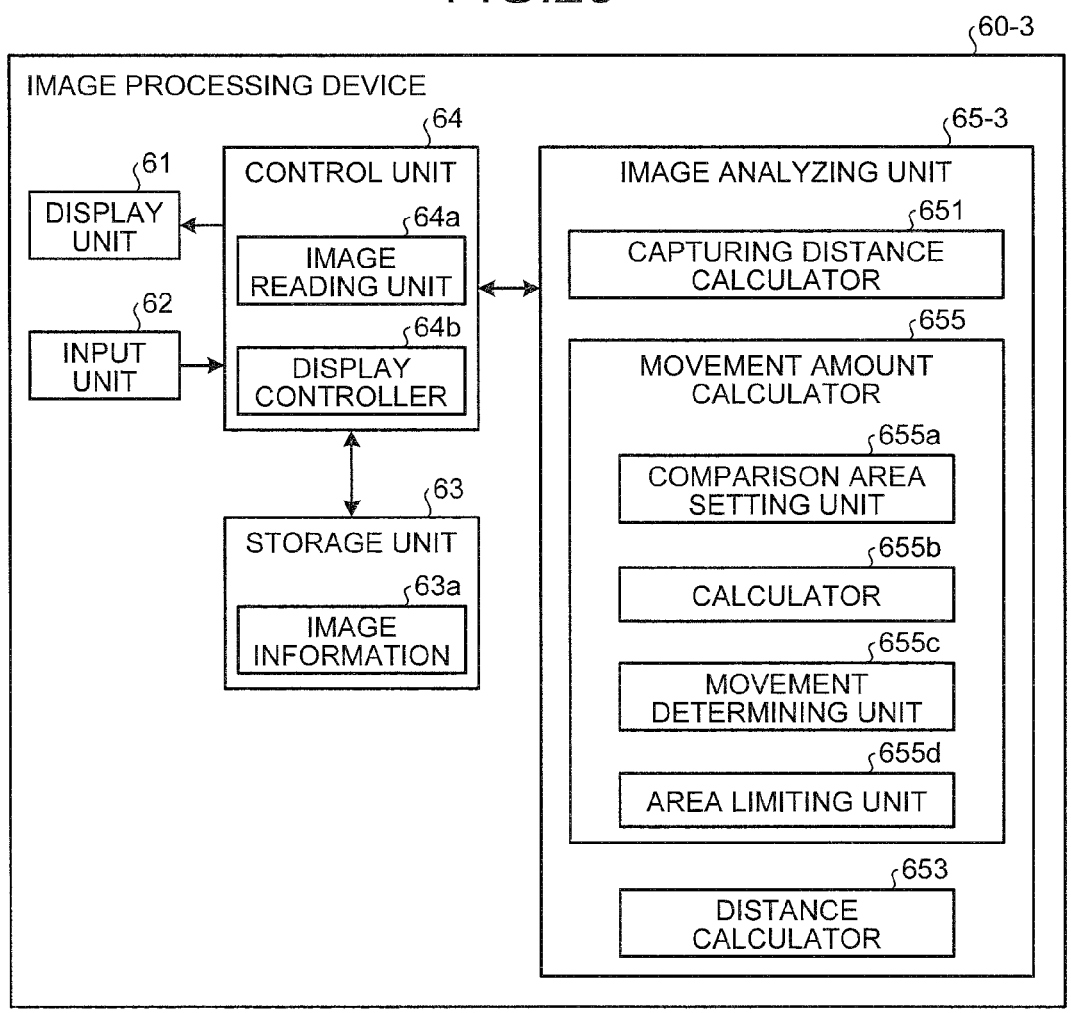
FIG. 20 is a block diagram showing a configuration of an image processing device according to a fourth embodiment.

For example, as shown in FIG. 20, an image processing device 60-3 according to the fourth embodiment is provided with an image analyzing unit 65-3 in place of the image analyzing unit 65 provided on the image processing device 60. The image analyzing unit 65-3 is provided with a movement amount calculator 655 in place of the movement amount calculator 652. The movement amount calculator 655 is provided with a comparison area setting unit 655a, a calculator 655b, a movement determining unit 655c and an area limiting unit 655d. Other configuration is the same as that of the image processing device 60, and the same reference numeral is given to the same component. Incidentally, the image processing device 60-3 may have a configuration in which the movement amount calculator 652 is provided with the area limiting unit 655d based on the configuration of the image processing device 60.

Figure 21:
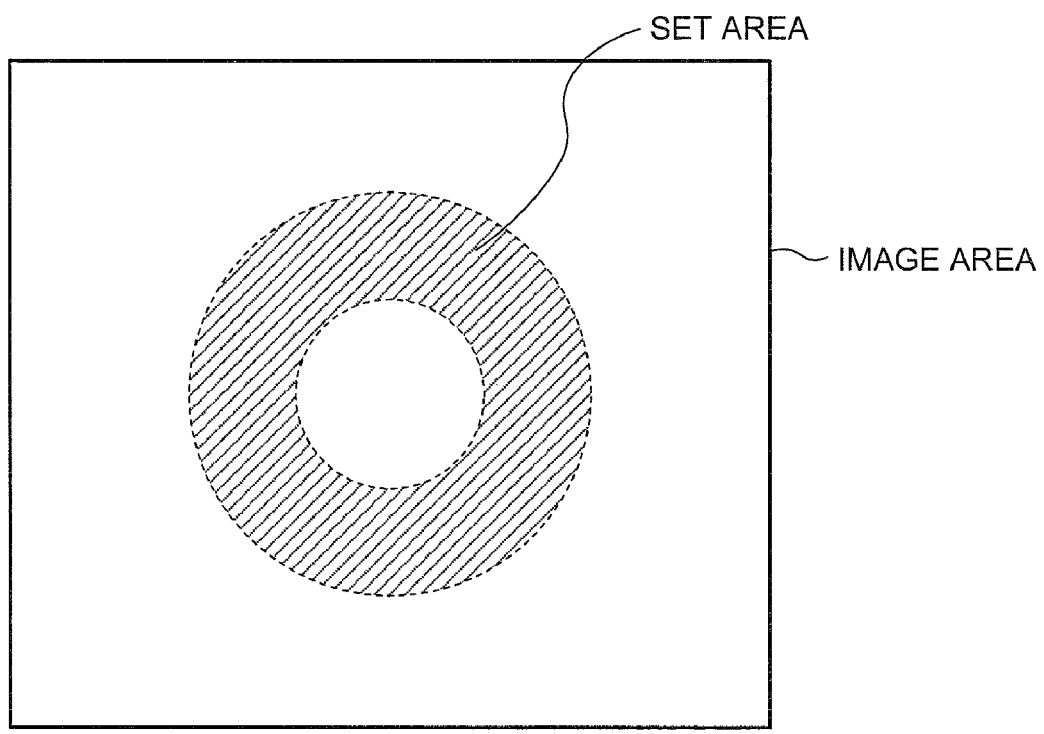
FIG. 21 is a view showing an example of a set area of a comparison area.

The area limiting unit 655d analyzes the image information 63a to limit the area in which the comparison area can be set in consideration of distortion and the like of the image. For example, the comparison area is set from the area other than a center of the image area and ends of the image area, as shown in FIG. 21. Incidentally, it is possible that the user sets an area selected in consideration of the distortion and the like of the image as the set area through the input unit 62.

The comparison area setting unit 655a sets the comparison area in an area limited by the area limiting unit 655d. The calculator 655b calculates the movement amount of the imaging device using the comparison area set by the comparison area setting unit 655a, as in the case of the calculator 652b. The movement determining unit 655c performs the process similar to that of the movement determining unit 652c.

Figure 22:
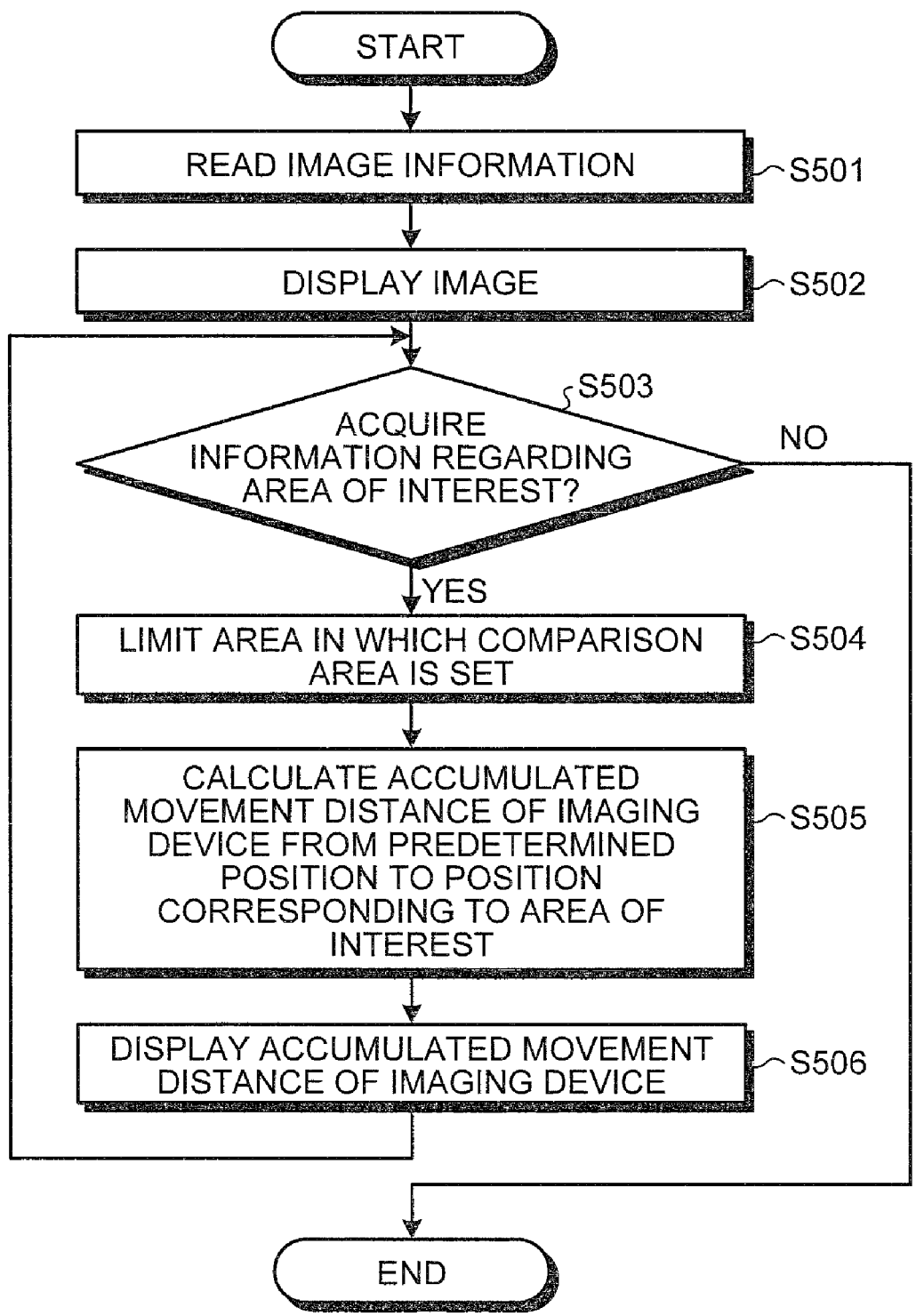
FIG. 22 is a flow chart showing an overview of an image analyzing process performed by the image processing device shown in FIG. 20.

Next, a procedure in which the image processing device 60-3 calculates to display the distance between the predetermined position and the area of interest under the control of the control unit 64 is described with reference to FIG. 22. First, as in steps S401 to S403, the image reading unit 64a reads the image information 63a from the storage unit 63 (step S501), the display controller 64b displays the image on the display unit 61 (step S502), and the control unit 64 accepts the input of the area of interest from the user (step S503). At step S503, it is possible to automatically set the area of interest as in step S403. When the control unit 64 acquires the information regarding the area of interest (step S503: Yes), the area limiting unit 655d limits the area in which the comparison area is set based on the image information or the instruction of the user (step S504). Thereafter, the image analyzing unit 65-3 calculates the accumulated movement distance of the imaging device from the predetermined position to the position corresponding to the area of interest (step S505), and the display controller 64b displays the accumulated movement distance calculated by the image analyzing unit 65-3 on the display unit 61 (step S506). Incidentally, when the control unit 64 does not acquire the information regarding the area of interest (step S503: No), the control unit 64 terminates the image analyzing process.

In this manner, the image processing device 60-3 according to the fourth embodiment sets the comparison area in the area limited in consideration of the distortion of the image or the instruction of the user. Therefore, in the fourth embodiment, the distance between the predetermined position and the area of interest can be calculated more correctly than in the case of the second or third embodiment.

Fifth Embodiment

Next, a fifth embodiment is described. In the fifth embodiment, an observation target captured in the image is specified and the distance of the imaging device from the predetermined position to the area of interest can be calculated for each observation target, in the image processing device according to the second to fourth embodiments.

Figure 23:
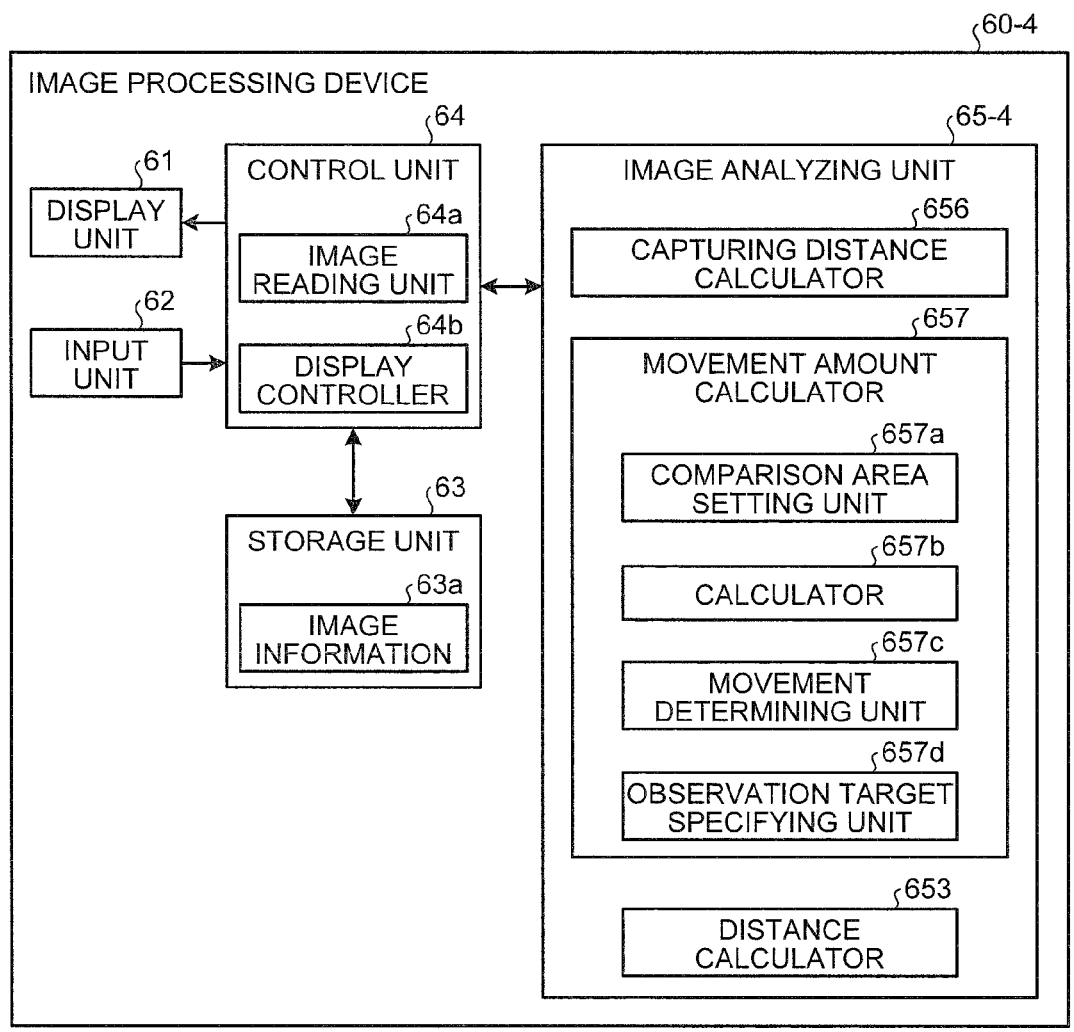
FIG. 23 is a block diagram showing a configuration of an image processing device according to a fifth embodiment.

For example, as shown in FIG. 23, an image processing device 60-4 according to the fifth embodiment is provided with an image analyzing unit 65-4 in place of the image analyzing unit 65 provided on the image processing device 60. The image analyzing unit 65-4 is provided with a capturing distance calculator 656 and a movement amount calculator 657 in place of the capturing distance calculator 651 and the movement amount calculator 652 provided on the image analyzing unit 65. The movement amount calculator 657 is provided with a comparison area setting unit 657a, a calculator 657b, a movement determining unit 657c and an observation target specifying unit 657d. Other configuration is the same as that of the image processing device 60, and the same reference numeral is given to the same component. Incidentally, the image processing device 60-4 may have a configuration obtained by adding the observation target specifying unit 657d to the movement amount calculator 652 based on the configuration of the image processing device 60. Alternatively, the image processing device 60-4 may have a configuration obtained by adding the observation target specifying unit 657d in place of the area limiting unit 655d of the movement amount calculator 655 based on the configuration of the image processing device 60-3.

The observation target specifying unit 657d specifies the observation target based on nature of a tract wall captured in each image, for example. Then, the capturing distance calculator 656 and the calculator 657b calculate the capturing distance between the imaging device and the area of interest and the movement amount of the imaging device, using a tract diameter corresponding to the observation target specified by the observation target specifying unit 657d and equations (6) and (7).

Incidentally, the comparison area setting unit 657a and the movement determining unit 657c perform the process similar to that of the comparison area setting unit 652a and the movement determining unit 652c.

Figure 24:
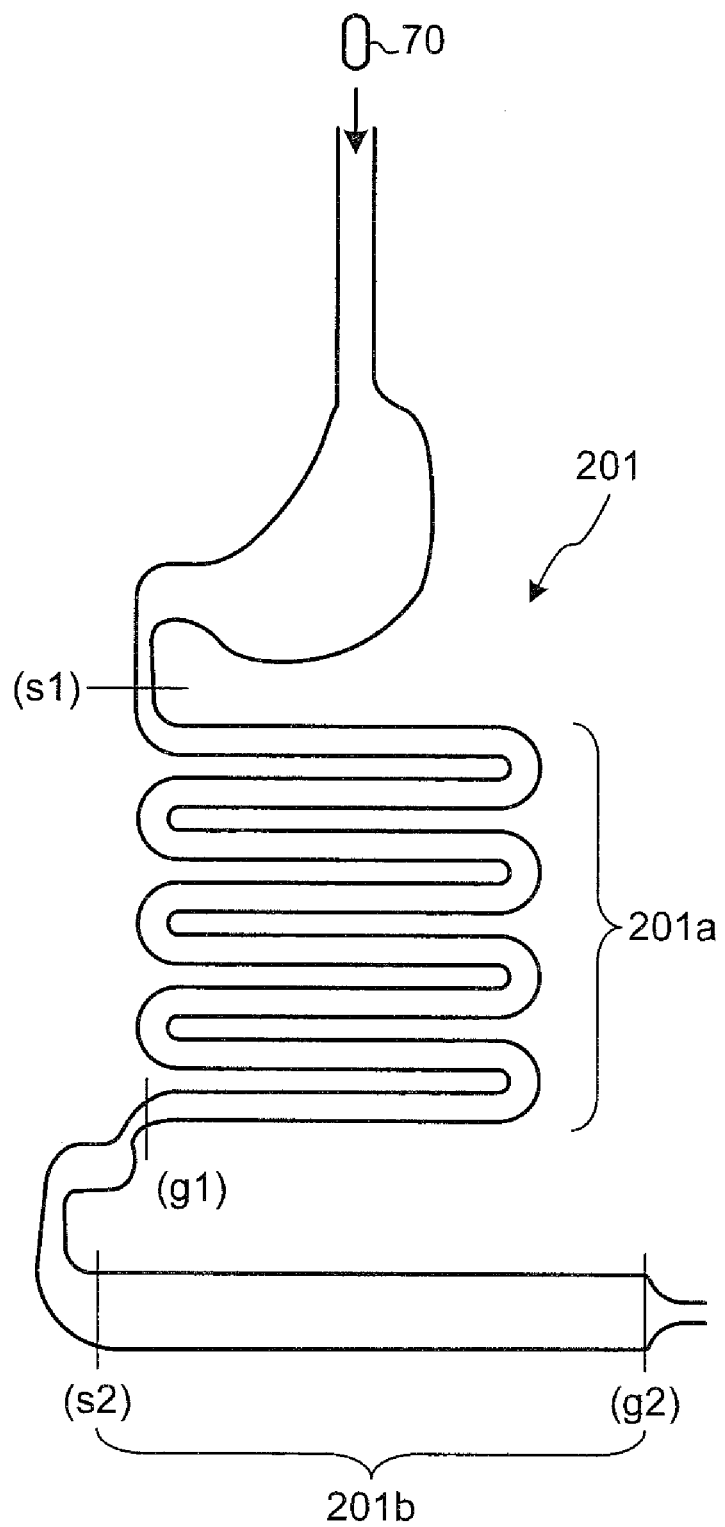
FIG. 24 is a view showing an example of a tract in which a plurality of observation targets is coupled.

Herein, a process in which the image analyzing unit 65-4 analyzes the row of images captured by an imaging device 70, which moves in a tract 201 having a plurality of observation targets is described with reference to FIG. 24. FIG. 24 is a view showing the tract 201 in which observation targets 201a and 201b having different tract diameters are coupled to each other. In FIG. 24, a portion between a predetermined position (s1) and a predetermined position (g1) of the tract 201 is the observation target 201a, and a portion between a predetermined position (s2) and a predetermined position (g2) is the observation target 201b. The imaging device 70 captures images in the tract 201 while moving in the order of the predetermined positions (s1), (g1), (s2) and (g2).

The observation target specifying unit 657d specifies whether the observation target captured in the image is the observation target 201a or the observation target 201b or this does not correspond to either of them based on the nature of the tract wall of the observation targets 201a and 201b. Further, the capturing distance calculator 656 calculates the capturing distance using the tract diameter corresponding to the specified observation target. Also, the calculator 657b calculates the movement amount of the imaging device 70 from the predetermined position set for each observation target, for example, from the predetermined positions (s1) and (s2), using the tract diameter corresponding to the observation target.

Figure 25:
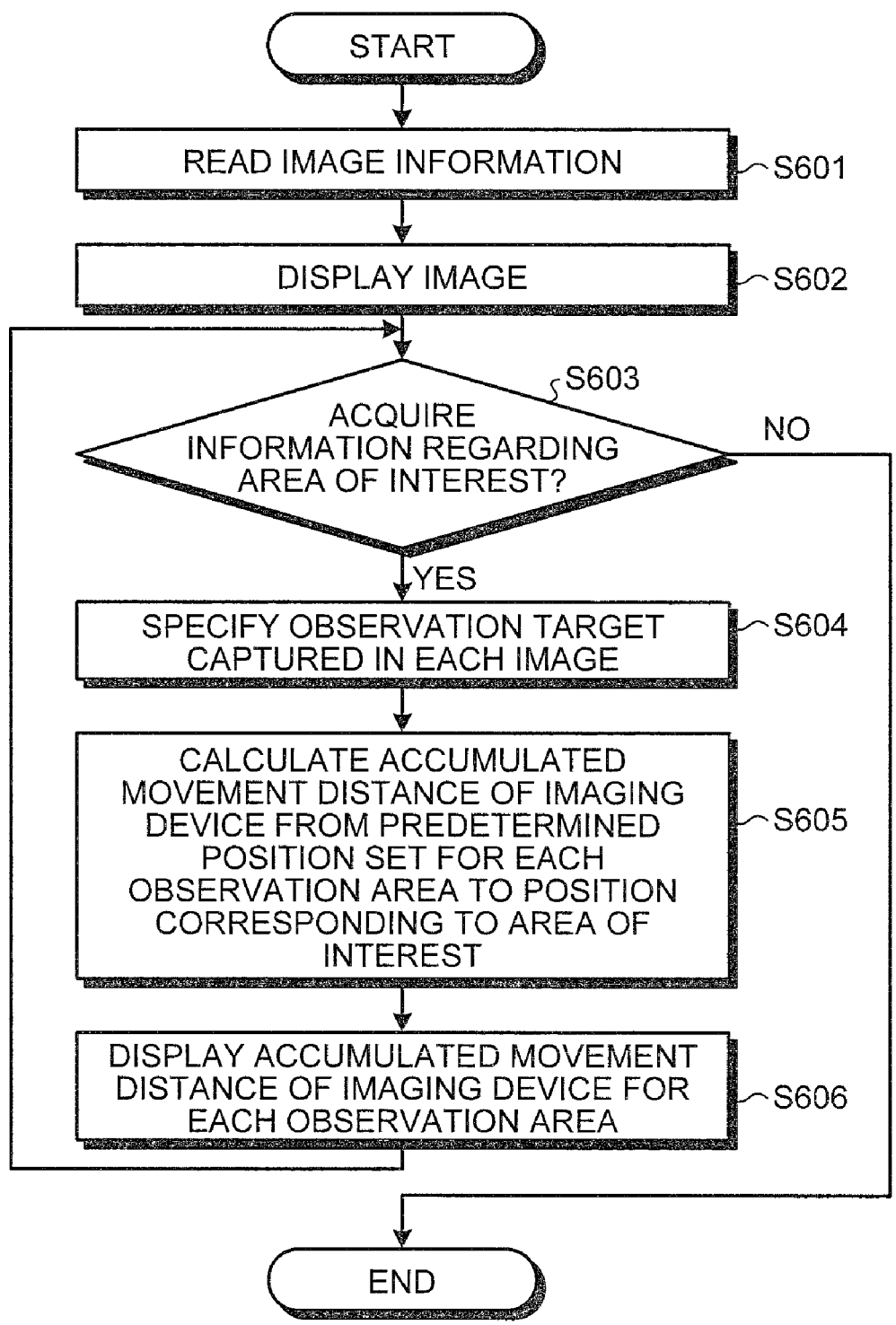
FIG. 25 is a flow chart showing an overview of an image analyzing process performed by the image processing device shown in FIG. 23.

Next, a procedure in which the image processing device 60-4 calculates to display the distance between the predetermined position and the area of interest under the control of the control unit 64 is described with reference to FIG. 25. First, as in steps S401 to S403, the image reading unit 64a reads the image information 63a from the storage unit 63 (step S601), the display controller 64b displays the image on the display unit 61 (step S602), and the control unit 64 accepts the input of the area of interest from the user (step S603). At step S603, it is possible to automatically set the area of interest as in step S403. When the control unit 64 acquires the information regarding the area of interest (step S603: Yes), the observation target specifying unit 657d specifies the observation target captured in each image based on the image information 63a (step S604). Thereafter, the image analyzing unit 65-4 calculates the accumulated movement distance of the imaging device from the predetermined position set for each observation target to the position corresponding to the area of interest (step S605), and the display controller 64b displays the calculated accumulated movement distance on the display unit 61 (step S606).

Incidentally, the predetermined position is determined for each observation target in this embodiment. For example, by specifying the observation target captured in each image, a position at which the observation targets are switched on the screen is specified. Then, the position at which the observation targets are switched on the screen is set as the predetermined position.

In this manner, the image processing device 60-4 according to the fifth embodiment automatically specifies the observation target captured in the image, and calculates the movement amount of the imaging device while changing the tract diameter, which is one of conditions when calculating the capturing distance and the movement amount, depending on the observation target. Therefore, in the fifth embodiment, the accumulated movement distance of the imaging device can be calculated using the images of the row of images captured in time series by the imaging device, which moves in the tract having the observation targets with different tract diameters. Also, it is possible to calculate the movement distance of the imaging device for each observation target by determining the predetermined position for each observation target.

Figure 26:
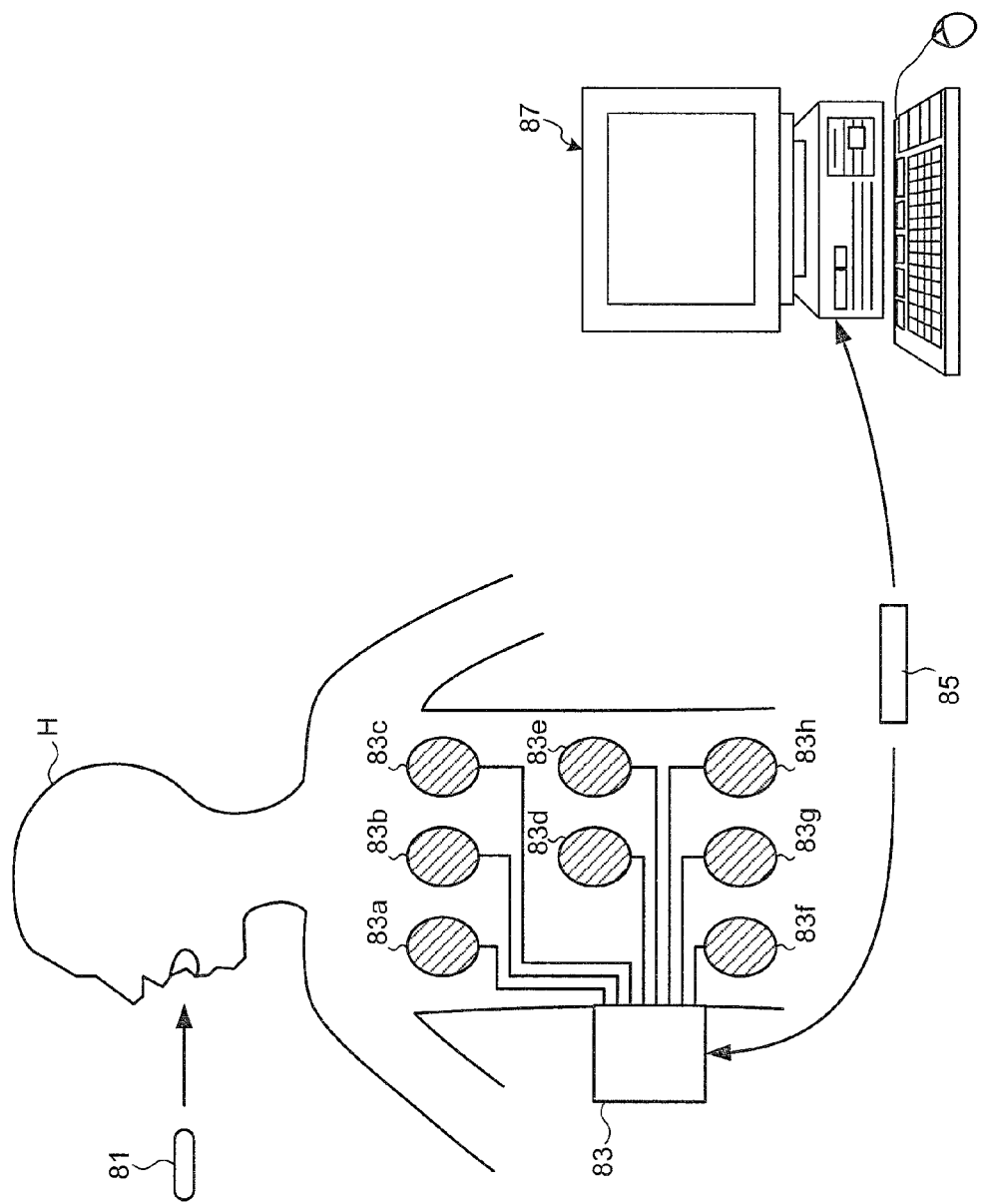
FIG. 26 is a view schematically showing a configuration example of an intra-gastrointestinal tract information acquiring system provided with the image processing device according to the fifth embodiment.

The image processing device according to the above-described second to fifth embodiments may be applied to the analysis of the row of images (row of intra-gastrointestinal tract images) captured by a capsule endoscope. FIG. 26 is a view schematically showing an example of an intra-gastrointestinal tract information acquiring system provided with an image processing device 87 of the fifth embodiment. An in-vivo information acquiring system shown in FIG. 26 is provided with a capsule endoscope 81 inserted into a gastrointestinal tract of a subject H for capturing intra-gastrointestinal tract images, a receiving device 83 for receiving wireless signals transmitted by the capsule endoscope 81 to accumulate images included in the received wireless signals, and a portable storage unit 85 such as a memory card attachable to and detachable from the receiving device 83 and the image processing device.

The capsule endoscope 81 has a capturing function for capturing the intra-gastrointestinal tract images, which is an example of the intraluminal image of the subject H, and a wireless communication function for transmitting the wireless signals including the captured images to outside. More specifically, the capsule endoscope 81 moves in the lumen such as the in-vivo gastrointestinal tract of the subject H, and at the same time, captures the intra-gastrointestinal tract images of the subject H at predetermined intervals of approximately 0.5 second (approximately 2 Hz), for example, and transmits the captured intra-gastrointestinal tract images to the receiving device 83 by a predetermined electric wave. The capsule endoscope 81 captures images while moving in the gastrointestinal tract of the subject H taking time of substantially 8 hours to create a row of intra-gastrointestinal tract images, which is an example of the time-series intraluminal images.

A plurality of receiving antennas 83a to 83h for receiving the wireless signals transmitted by the capsule endoscope 81 are connected to the receiving device 83. The receiving antennas 83a to 83h are constructed using a loop antenna, for example, and are randomly arranged on the body surface of the subject H so as to correspond to a passage route of the capsule endoscope 81. The number of such receiving antenna to be arranged for the subject H is one or more, and the number of arrangement is not limited to eight as shown.

The receiving device 83 receives the wireless signals transmitted from the capsule endoscope 81 through any one of the receiving antennas 83a to 83h and acquires the image information of the intra-gastrointestinal tract images of the subject H based on the received wireless signals. The image information obtained by the receiving device 83 is stored in the storage unit 85 inserted into the receiving device 83. The storage unit 85 storing the image information of the intra-gastrointestinal tract images of the subject H is inserted into the image processing device 87 and used in the process in the image processing device 87.

The image processing device 87 is provided with the observation target specifying unit 657d described with reference to FIG. 23, and can specify each organ captured by the capsule endoscope 81. Therefore, according to the image processing device 87, the movement distance of the imaging device can be calculated for each organ.

Incidentally, the observation target specifying unit specifies each organ based on the nature of the surface of the mucosal membrane of the gastrointestinal tract. The nature of the surface of the mucosal membrane of the gastrointestinal tract is different among organs: the mucosal membrane surface of the esophagus and the stomach is flat with irregularity less than that of the small intestine, and the mucosal membrane surface of the small intestine has much irregularity due to villus or the like. Thus, low-frequency components are dominant in the image in which the esophagus and the stomach are captured, and high-frequency components are dominant in the image in which the small intestine is captured. Therefore, the observation target specifying unit determines the organ captured in the observation image utilizing spatial-frequency components in each image. Specifically, the observation target specifying unit determines the organ using a power spectrum obtained by Fourier transformation, for example, as spatial-frequency component information.

Also, due to the difference in nature of the mucosal membrane surface of each organ, there is difference in strength of correlation between the predetermined pixel and surrounding pixels of each image, a texture information amount of each image, a file size of compressed data of each image, or a DCT coefficient calculated when expanding the compressed data between the organs captured in each image. Therefore, the observation target specifying unit may determine the organ by comparing them. Also, since a moving speed of the capsule endoscope is different between the organs, the change amount of the frequency component is different between the time-series continuous images, so that the change amount of the file size of the compressed data or the change amount of the DCT coefficient are different between the images. Then, the observation target specifying unit may determine the organ by comparing the change amounts between the images.

When the doctor browses the row of intra-gastrointestinal tract images and finds out a lesion, the information of the distance between the lesion and the entrance or the exit of each organ is effective information when treating the lesion and making a treatment plan. In this manner, according to the intra-gastrointestinal tract information acquiring system of this embodiment, the information useful to the doctor can be provided.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device for processing time-series intraluminal images captured by an imaging device moving in an in-vivo lumen, the image processing device comprising:
   a structural area extracting unit that extracts a structural area from the intraluminal image;
   a corresponding area extracting unit that extracts a corresponding area corresponding to the structural area from the intraluminal image at a second time point different from a first time point at which the structural area is extracted;
   a lumen deep portion extracting unit that extracts a lumen deep portion, on which a deep portion in the lumen is captured, from the intraluminal image; and
   a movement amount estimating unit that estimates a movement amount of the imaging device based on positions of the structural area, the corresponding area and the lumen deep portion.

2. The image processing device according to claim 1, wherein the movement amount estimating unit obtains a first projected distance by projecting a first distance from the imaging device to the structural area at the first time point on an intraluminal wall surface using the positions of the structural area, the corresponding area and the lumen deep portion, and obtains a second projected distance by projecting a second distance from the imaging device to the corresponding area at the second time point on the intraluminal wall surface, and further calculates a difference between the first projected distance and the second projected distance to estimate the movement amount of the imaging device.

3. The image processing device according to claim 2, wherein the movement amount estimating unit calculates a first angle, which is an angle between a vector from an optical center corresponding to a main point of an optical system of the imaging device to the lumen deep portion and a vector from the optical center to the structural area at the first time point, to obtain the first projected distance using the calculated first angle and a radius of the lumen, and calculates a second angle, which is an angle between the vector from the optical center corresponding to the main point of the optical system of the imaging device to the lumen deep portion and the vector from the optical center to the corresponding area at the second time point, to obtain the second projected distance using the calculated second angle and the radius of the lumen.

4. The image processing device according to any one of claims 1 to 3, wherein the structural area extracting unit extracts an area, in which a mucosal membrane in the lumen is captured, as the structural area.

5. The image processing device according to claim 1, wherein the structural area extracting unit extracts an area, in which at least one of wrinkles of the mucosal membrane in the lumen and blood vessels on a surface of the mucosal membrane in the lumen are captured, as the structural area.

6. The image processing device according to claim 1, wherein the structural area extracting unit extracts an area having a distribution area of pixel values larger than a predetermined threshold as the structural area.

7. The image processing device according to claim 1, wherein the structural area extracting unit extracts a plurality of areas in the intraluminal image as the structural areas.

8. The image processing device according to claim 1, wherein the corresponding area extracting unit performs a matching process by setting the structural area as a template on the in-vivo intraluminal images at different time points and extracts an area having similarity at the time of the matching higher than a predetermined threshold as the corresponding area.

9. The image processing device according to claim 1, wherein the lumen deep portion extracting unit extracts an area, in which dark pixels are gathered in the intraluminal image, as the lumen deep portion.

10. The image processing device according to claim 1, further comprising a position estimating unit that estimates a position of the imaging device in the lumen at each time when capturing each intraluminal image by accumulating a plurality of values of the movement amount estimated by processing a plurality of the intraluminal images.

11. A computer readable storage device storing an image processing program that, when executed by a computer for processing time-series intraluminal images captured by an imaging device moving in an in-vivo lumen, causes the computer to perform:
    a structural area extracting process that extracts a structural area from the intraluminal image;
    a corresponding area extracting process that extracts a corresponding area corresponding to the structural area from the intraluminal image at a second time point different from a first time point at which the structural area is extracted;
    a lumen deep portion extracting process that extracts a lumen deep portion, on which a deep portion in the lumen is captured, from the intraluminal image; and
    a movement amount estimating process that estimates a movement amount of the imaging device based on positions of the structural area, the corresponding area and the lumen deep portion.

12. An image processing method for processing time-series intraluminal images captured by an imaging device moving in an in-vivo lumen, the method comprising:
- a structural area extracting step that extracts a structural area from the intraluminal image;
- a corresponding area extracting step that extracts a corresponding area corresponding to the structural area from the intraluminal image at a second time point different from a first time point at which the structural area is extracted;
- a lumen deep portion extracting step that extracts a lumen deep portion, on which a deep portion in the lumen is captured, from the intraluminal image; and
- a movement amount estimating step that estimates, using an image processing device, a movement amount of the imaging device based on positions of the structural area, the corresponding area and the lumen deep portion.

* * * * *